US010087462B2

(12) United States Patent
Bhattacharyya et al.

(10) Patent No.: US 10,087,462 B2
(45) Date of Patent: Oct. 2, 2018

(54) ***ARABIDOPSIS* NONHOST RESISTANCE GENE(S) AND USE THEREOF TO ENGINEER SDS RESISTANT PLANTS**

(71) Applicant: Iowa State University Research Foundation, Inc., Ames, IA (US)

(72) Inventors: Madan K. Bhattacharyya, Ames, IA (US); Prashant Singh, Ames, IA (US); Sekhar Kambakam, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 227 days.

(21) Appl. No.: 14/989,634

(22) Filed: Jan. 6, 2016

(65) Prior Publication Data

US 2016/0201081 A1 Jul. 14, 2016

Related U.S. Application Data

(60) Provisional application No. 62/100,306, filed on Jan. 6, 2015.

(51) Int. Cl.

| | |
|---|---|
| *C12N 15/82* | (2006.01) |
| *A01H 5/00* | (2018.01) |
| *C07K 14/415* | (2006.01) |

(52) U.S. Cl.

CPC .......... *C12N 15/8282* (2013.01); *A01H 5/00* (2013.01); *C07K 14/415* (2013.01)

(58) Field of Classification Search

CPC .............. C07K 14/415; C12N 15/8279; C12N 15/8282; C12N 15/8281; A01H 5/10

See application file for complete search history.

(56) References Cited

U.S. PATENT DOCUMENTS

| | | | | |
|---|---|---|---|---|
| 2006/0107345 A1 | 5/2006 | Alexandrov et al. | | |
| 2007/0039071 A1* | 2/2007 | Chang | C07K 14/415 | 800/284 |
| 2007/0294782 A1* | 12/2007 | Abad | C12N 15/8261 | 800/278 |
| 2012/0222167 A1 | 8/2012 | Li et al. | | |

FOREIGN PATENT DOCUMENTS

| | | | |
|---|---|---|---|
| WO | WO2001035726 A1 * | 5/2001 | |
| WO | WO2001035726 A1 * | 5/2001 | A01H 1/00 |
| WO | 2014117988 A1 | 8/2014 | |
| WO | 2014117990 A1 | 8/2014 | |

OTHER PUBLICATIONS

Becker, Annette, et al. "Ancestry and diversity of BEL1-like homeobox genes revealed by gymnosperm (Gnetum gnemon) homologs." Development Genes and Evolution 212.9 (2002): 452-457 (Year: 2002).*

Friedberg, Iddo. "Automated protein function prediction—the genomic challenge." Briefings in bioinformatics 7.3 (2006): 225-242. (Year: 2006).*

Lamesch, Philippe, et al. "The *Arabidopsis* Information Resource (TAIR): improved gene annotation and new tools." Nucleic acids research 40.D1 (2011): D1202-D1210 (Year: 2011).*

Collins, Nicholas C., et al., "SNARE-protein-mediated disease resistance at the plant cell war", NATURE, (2003), vol. 425, pp. 973-977.

Kang, Li, et al., "Interplay of the *Arabidopsis* nonhost resistance gene NH01 with bacterial virulence", PNAS, (2003), vol. 100, No. 6, pp. 3519-3524.

Kuc, Joseph, "Molecular aspects of plant responses to pathogens", ACTA, (1997), vol. 19, No. 4, pp. 551-559.

Sumit, Rishi, et al., "*Arabidopsis* nonhost resistance gene PSS1 confers immunity against an oomycete and a fungal pathogen but not a bacterial pathogen that cause diseases in soybean", BMC Plant Biology, (2012), vol. 12, No. 87, 14 pages.

* cited by examiner

*Primary Examiner* — Lee A Visone
*Assistant Examiner* — Weihua Fan
(74) *Attorney, Agent, or Firm* — McKee, Voorhees & Sease, PLC

(57) ABSTRACT

The present invention relates to a method of increasing resistance against plant pathogens, particularly *Fusarium virguliforme* and *Phytophthora sojae* in transgenic plants and/or plant cells, through the use of non host resistance nucleic acid molecules isolated from *Arabidopsis*. In these plants, at least one nonhost *Arabidopsis* resistance protein is introduced in comparison to the wild-type plants to confer resistance to plant pathogens. The invention relates to transgenic plants and/or plant cells having increased resistance to plant pathogens, particularly *Fusarium virguliforme* and *Phytophthora sojae*, to expression vectors, transformed plants and plant cells as well as the use of such plants in a plant breeding program.

6 Claims, 11 Drawing Sheets

Specification includes a Sequence Listing.

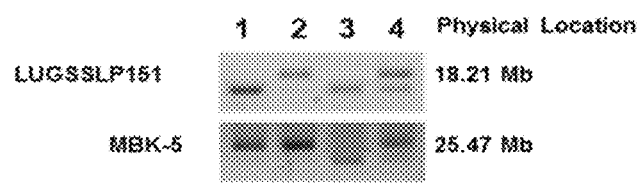
FIG. 2A
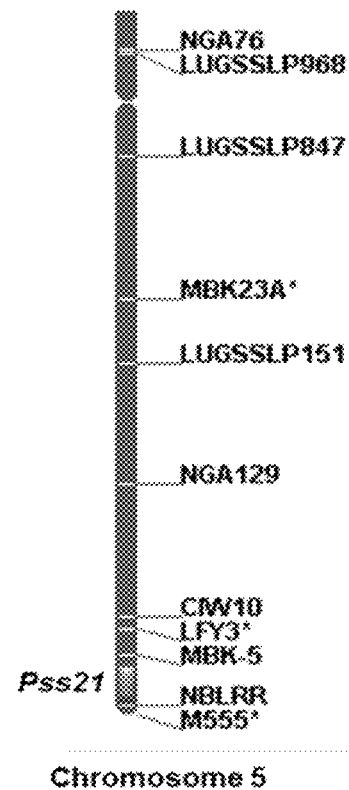
FIG. 2B
FIG. 2C

| pss25F$_{2:3}$ | Molecular Marker | | | | |
|---|---|---|---|---|---|
| | SBP4_12.5 | SBP4_14.0 | SBP5_16.06 | NGA1139 | NGA1107 |
| 25-44-15 | A | A | A | A | A |
| 25-42-8 | H | H | A | A | H |
| 25-101-7 | A | A | A | A | A |
| 25-101-8 | A | A | A | A | A |
| 25-42-13 | A | A | A | A | H |
| 25-43-7 | A | A | A | A | A |
| 25-3-X | H | H | A | A | H |
| 25-15-17 | B | B | A | A | H |
| 25-42-43 | H | A | A | A | A |
| 25-8-3 | A | A | A | A | A |
| 25-106-22 | H | H | A | A | H |
| 25-7-8A | A | A | A | A | A |
| 25-105-7 | H | H | A | A | H |
| 25-8-32 | H | H | A | H | H |
| 25-42-2B | A | A | A | H | H |

Map of chromosome4 (*arabidopsis*) showing the location of pss6 (orange) and different markers.

ion. The government has certain rights in the invention.

SEQUENCE LISTING

<160> NUMBER OF SEQ ID NOS: 6

<210> SEQ ID NO 1
<211> LENGTH: 842
<212> TYPE: DNA
<213> ORGANISM: Arabidopsis

<400> SEQUENCE: 1

```
gtggcgactc aaatgggtca agaatcgttt atctatagct tcgtcgccag aggaactatg      60
atcctcgccg agtataccga attcacaggc aatttcccgt ctattgctgc tcagtgtctc     120
cagaagcttc cgtcctccag caacagcaag ttcacttaca actgcgatca ccataccttc     180
aatttccttg tcgaagatgg ctacgcatat tgtgttgtgg cgaaagattc tcttagcaag     240
caaatctcga tcgcatttct ggagcgtgtg aaagctgatt tcaagaagag atatggaggt     300
ggaaaagcaa gtacagctat cgccaaaagt ctcaacaagg agttcgggcc ggtgatgaag     360
gaacacatga attatattgt tgaccatgca gaggagattg aaaaactaat aaaagtcaag     420
gctcaggttt cagaagttaa aagtataatg ttggagaata ttgacaaggc aatcgacaga     480
ggggaaaatc taacagttct tactgacaag accgagaatc tacgctctca ggcgcaggaa     540
tacaagaaac aagggacaca ggtgaggagg aaattgtggt accagaacat gaagataaaa     600
ctggtggttc ttgggatctt gctactactt gttctcataa tctggatatc ggtttgtcat     660
ggatttaatt gcacggattg aagacacaac aaatcactct acgtgatggt tagagactta     720
gagcttttgg cggagacagg cgacaaacag agacaaaagt cttcagtaga gagattagta     780
aagagagaga gagggaaca aaatggtacc atatgtattg taaggttttg actttggatg     840
tt                                                                    842
```

<210> SEQ ID NO 2
<211> LENGTH: 222
<212> TYPE: PRT
<213> ORGANISM: Arabidopsis

<400> SEQUENCE: 2

```
Met Gly Gln Glu Ser Phe Ile Tyr Ser Phe Val Ala Arg Gly Thr Met
1               5                   10                  15

Ile Leu Ala Glu Tyr Thr Glu Phe Thr Gly Asn Phe Pro Ser Ile Ala
```

```
                    20                  25                  30
Ala Gln Cys Leu Gln Lys Leu Pro Ser Ser Asn Ser Lys Phe Thr
                35                  40                  45
Tyr Asn Cys Asp His His Thr Phe Asn Phe Leu Val Glu Asp Gly Tyr
        50                  55                  60
Ala Tyr Cys Val Val Ala Lys Asp Ser Leu Ser Lys Gln Ile Ser Ile
65                  70                  75                  80
Ala Phe Leu Glu Arg Val Lys Ala Asp Phe Lys Lys Arg Tyr Gly Gly
                85                  90                  95
Gly Lys Ala Ser Thr Ala Ile Ala Lys Ser Leu Asn Lys Glu Phe Gly
                100                 105                 110
Pro Val Met Lys Glu His Met Asn Tyr Ile Val Asp His Ala Glu Glu
                115                 120                 125
Ile Glu Lys Leu Ile Lys Val Lys Ala Gln Val Ser Glu Val Lys Ser
                130                 135                 140
Ile Met Leu Glu Asn Ile Asp Lys Ala Ile Asp Arg Gly Glu Asn Leu
145                 150                 155                 160
Thr Val Leu Thr Asp Lys Thr Glu Asn Leu Arg Ser Gln Ala Gln Glu
                165                 170                 175
Tyr Lys Lys Gln Gly Thr Gln Val Arg Arg Lys Leu Trp Tyr Gln Asn
                180                 185                 190
Met Lys Ile Lys Leu Val Val Leu Gly Ile Leu Leu Leu Leu Val Leu
                195                 200                 205
Ile Ile Trp Ile Ser Val Cys His Gly Phe Asn Cys Thr Asp
210                 215                 220

<210> SEQ ID NO 3
<211> LENGTH: 2768
<212> TYPE: DNA
<213> ORGANISM: Arabidopsis

<400> SEQUENCE: 3
gccaacaaac aacaagtctt caccttcttc ttcttcttct tcttcaaaat ctcttgtacg      60
caaataatcc atgagaaact agggtttaac ttgagatctc tcttccgaag tattaccatc     120
aatggcgact tcttcttctt catcgtcgtc tctgcttttta ccaaacatca atttcaactc     180
aagacaatct ccaacaatca ctcgttccgt ttcaatcgcc gggatcttct tacccagaaa     240
ccgattaagc tacaatcaca atctccggat tcgtacgaga ttaatcagag cttctaaaga     300
cgataatgtc gctgttgaag atcgtgataa tgcagtgaag atcaacggtg attacaacgg     360
aagtgcacgt ttaacggta acggctctgc gagaaaatcc gtcaacggag atttttaacgg     420 aagtgctcgt ttgaacggta acggtagttt ggtgaagtat gtgaacggaa gtgtaacggt     480
ggaaacggag gaagtgacaa agaagagaaa agaagaagtg aggaagaaga gagtagaaga     540
tattggtcaa gaggatgctt ggtttaagaa caacactcaa caaaaacaag ttgaggtttc     600
tgttacacct ggtggtcgat ggaatagatt caagacttac tcaactattc aaagaacatt     660
ggagatttgg ggttttgttg tacagtttat tttcaggact tggttaagca ataagaagtt     720
ctcttataaa gggggaatga ctgaagagaa gaaggtttta agaggaaggt ttttggctaa     780
gtggttgaaa gaaaacattt tgagattagg tcctacattt atcaaaattg gcaacagtt     840 ctctactaga gtggatattc ttcctcaaga gtatgttgat caattgtcag aacttcagga     900
tcaagttcct cctttccctt ctgctacagc tttatccatt gttgaagagg agcttggagg     960
ttctgttgag gacatttcg accgttttga ttatgaacct atagctgcag ctagtcttgg    1020
```

```
gcaagttcac cgtgcaagac ttaagggtca agaggttgtc cttaaagtac agagacctgg    1080
tctgaaggat ctctttgata ttgacccttaa gaatttgagg gtgatcgctg agtatctcca    1140
aaaggtggac ccaaaatcag atggtgcaaa gagagattgg gttgcaatct atgatgaatg    1200
tgccagtgtt ttgtaccagg aaattgatta cacaaaagaa gcagctaatt cggagttgtt    1260
tgctaataac ttcaaagact tagagtatgt aaaagttcca tccatctact gggaatacac    1320
tacacctcag gtcctgacaa tggagtatgt ccctgggatt aagattaaca agatacaagc    1380
cttagatcag ttaggtgttg atcgaaaaag gctaggaaga tatgctgttg aatcttacct    1440
ggagcaaatc ttatctcatg gattcttcca cgccgaccct cacccctggga atatagcagt    1500 tgatgatgtc aatggcgggc ggctgatatt ttacgacttt ggaatgatgg gaagtattag    1560
cccaaatatt agagaaggtt tgttggaggc atttatggc gtctatgaaa aggatccaga    1620
taaggtcctt caagctatgg ttcaaatggg agtgcttgta ccaactggag atttgacggc    1680
agttagaaga acagcattgt ttttctcaa cagttttgaa gagcggcttg ctgcacaaag    1740
aaaggagaaa gaagaaatag cagcagcaga agagcttggg ttcaagaagc cactaagcaa    1800
ggaagaaaag caagagaaaa agaagcaaag gttggctgca atcggagaag acttattagc    1860
cattgcggct gatcagcctt tccggttccc cgccacattc acatttgttg ttagagcctt    1920
ttcagtattg gatggcatcg gcaaaggtct tgacccccga tttgatataa cggagattgc    1980
taaaccctat gctttggaat tgttgcggtt tcgggaagct ggagtggaag ttgtagtaaa    2040
ggacctgaga aagagatggg acaggcaatc acaagcattc tacaatctat ttagacaagc    2100
ggatagagtt gaaaagctag ctgtagtcat tgaacgactt gagcaaggtg atttgaagct    2160
tagggtccga gcgctagagt ctgagagggc atttcaacgc gttgcagctg ttcaaaaaaac    2220 agtaggaagt gctgttgctg caggaagttt agtcaatctc gcaacaattt tgtatctgaa    2280
ttctataaaa acacctgcaa ctatagcata tacagtatgt gctttcttca gcctccaagt    2340
tctaatcgga atcataaagg ttaagaagtt cgatcaacgg gaaaaactaa tcactggaac    2400
agcttaagaa cttgcttgaa gaaatgtatt aaagcttctt caatctccat aaacccttt    2460 gtgcatttca caggagtgtt aacaatttca ctggtctgca aataaaatta tcttatggaa    2520
gcttgagagg caagagatgg tcaactagtc aaaccaccac cactctctca tctctgtctt    2580
cttaaagttc gataataatt tttggagagg agactctggt tgttcatcaa cagagtggtc    2640
atgagccaca tgtattgctt gtgtatagag agatttagaa attaggaact ttttcgtata    2700
aatatactca ttgtactcag ctactcacta gactcatctc tgttttagta ataaaaaaaa    2760
aaaaaaaa                                                              2768
```

<210> SEQ ID NO 4
<211> LENGTH: 761
<212> TYPE: PRT
<213> ORGANISM: Arabidopsis

<400> SEQUENCE: 4

```
Met Ala Thr Ser Ser Ser Ser Ser Ser Leu Leu Leu Pro Asn Ile
1               5                   10                  15

Asn Phe Asn Ser Arg Gln Ser Pro Thr Ile Thr Arg Ser Val Ser Ile
                20                  25                  30

Ala Gly Ile Phe Leu Pro Arg Asn Arg Leu Ser Tyr Asn His Asn Leu
            35                  40                  45

Arg Ile Arg Thr Arg Leu Ile Arg Ala Ser Lys Asp Asp Asn Val Ala
```

-continued

```
                50                  55                  60
Val Glu Asp Arg Asp Asn Ala Val Lys Ile Asn Gly Asp Tyr Asn Gly
 65                  70                  75                  80

Ser Ala Arg Leu Asn Gly Asn Gly Ser Ala Arg Lys Ser Val Asn Gly
                 85                  90                  95

Asp Phe Asn Gly Ser Ala Arg Leu Asn Gly Asn Gly Ser Leu Val Lys
                100                 105                 110

Tyr Val Asn Gly Ser Val Thr Val Glu Thr Glu Val Thr Lys Lys
                115                 120                 125

Arg Lys Glu Glu Val Arg Lys Arg Val Glu Asp Ile Gly Gln Glu
                130                 135                 140

Asp Ala Trp Phe Lys Asn Asn Thr Gln Gln Lys Gln Val Glu Val Ser
145                 150                 155                 160

Val Thr Pro Gly Gly Arg Trp Asn Arg Phe Lys Thr Tyr Ser Thr Ile
                165                 170                 175

Gln Arg Thr Leu Glu Ile Trp Gly Phe Val Val Gln Phe Ile Phe Arg
                180                 185                 190

Thr Trp Leu Ser Asn Lys Lys Phe Ser Tyr Lys Gly Gly Met Thr Glu
                195                 200                 205

Glu Lys Lys Val Leu Arg Arg Lys Val Leu Ala Lys Trp Leu Lys Glu
                210                 215                 220

Asn Ile Leu Arg Leu Gly Pro Thr Phe Ile Lys Ile Gly Gln Gln Phe
225                 230                 235                 240

Ser Thr Arg Val Asp Ile Leu Pro Gln Glu Tyr Val Asp Gln Leu Ser
                245                 250                 255

Glu Leu Gln Asp Gln Val Pro Pro Phe Pro Ser Ala Thr Ala Leu Ser
                260                 265                 270

Ile Val Glu Glu Glu Leu Gly Gly Ser Val Glu Asp Ile Phe Asp Arg
                275                 280                 285

Phe Asp Tyr Glu Pro Ile Ala Ala Ala Ser Leu Gly Gln Val His Arg
                290                 295                 300

Ala Arg Leu Lys Gly Gln Glu Val Val Leu Lys Val Gln Arg Pro Gly
305                 310                 315                 320

Leu Lys Asp Leu Phe Asp Ile Asp Leu Lys Asn Leu Arg Val Ile Ala
                325                 330                 335

Glu Tyr Leu Gln Lys Val Asp Pro Lys Ser Asp Gly Ala Lys Arg Asp
                340                 345                 350

Trp Val Ala Ile Tyr Asp Glu Cys Ala Ser Val Leu Tyr Gln Glu Ile
                355                 360                 365

Asp Tyr Thr Lys Glu Ala Ala Asn Ser Glu Leu Phe Ala Asn Asn Phe
                370                 375                 380

Lys Asp Leu Glu Tyr Val Lys Val Pro Ser Ile Tyr Trp Glu Tyr Thr
385                 390                 395                 400

Thr Pro Gln Val Leu Thr Met Glu Tyr Val Pro Gly Ile Lys Ile Asn
                405                 410                 415

Lys Ile Gln Ala Leu Asp Gln Leu Gly Val Asp Arg Lys Arg Leu Gly
                420                 425                 430

Arg Tyr Ala Val Glu Ser Tyr Leu Glu Gln Ile Leu Ser His Gly Phe
                435                 440                 445

Phe His Ala Asp Pro His Pro Gly Asn Ile Ala Val Asp Asp Val Asn
                450                 455                 460

Gly Gly Arg Leu Ile Phe Tyr Asp Phe Gly Met Met Gly Ser Ile Ser
465                 470                 475                 480
```

```
Pro Asn Ile Arg Glu Gly Leu Leu Glu Ala Phe Tyr Gly Val Tyr Glu
            485                 490                 495
Lys Asp Pro Asp Lys Val Leu Gln Ala Met Val Gln Met Gly Val Leu
        500                 505                 510
Val Pro Thr Gly Asp Leu Thr Ala Val Arg Arg Thr Ala Leu Phe Phe
    515                 520                 525
Leu Asn Ser Phe Glu Glu Arg Leu Ala Ala Gln Arg Lys Glu Lys Glu
530                 535                 540
Glu Ile Ala Ala Ala Glu Glu Leu Gly Phe Lys Lys Pro Leu Ser Lys
545                 550                 555                 560
Glu Glu Lys Gln Glu Lys Lys Gln Arg Leu Ala Ala Ile Gly Glu
            565                 570                 575
Asp Leu Leu Ala Ile Ala Ala Asp Gln Pro Phe Arg Phe Pro Ala Thr
        580                 585                 590
Phe Thr Phe Val Val Arg Ala Phe Ser Val Leu Asp Gly Ile Gly Lys
    595                 600                 605
Gly Leu Asp Pro Arg Phe Asp Ile Thr Glu Ile Ala Lys Pro Tyr Ala
610                 615                 620
Leu Glu Leu Leu Arg Phe Arg Glu Ala Gly Val Glu Val Val Lys
625                 630                 635                 640
Asp Leu Arg Lys Arg Trp Asp Arg Gln Ser Gln Ala Phe Tyr Asn Leu
            645                 650                 655
Phe Arg Gln Ala Asp Arg Val Glu Lys Leu Ala Val Val Ile Glu Arg
        660                 665                 670
Leu Glu Gln Gly Asp Leu Lys Leu Arg Val Arg Ala Leu Glu Ser Glu
    675                 680                 685
Arg Ala Phe Gln Arg Val Ala Ala Val Gln Lys Thr Val Gly Ser Ala
690                 695                 700
Val Ala Ala Gly Ser Leu Val Asn Leu Ala Thr Ile Leu Tyr Leu Asn
705                 710                 715                 720
Ser Ile Lys Thr Pro Ala Thr Ile Ala Tyr Thr Val Cys Ala Phe Phe
            725                 730                 735
Ser Leu Gln Val Leu Ile Gly Ile Ile Lys Val Lys Phe Asp Gln
        740                 745                 750
Arg Glu Lys Leu Ile Thr Gly Thr Ala
        755                 760

<210> SEQ ID NO 5
<211> LENGTH: 4966
<212> TYPE: DNA
<213> ORGANISM: Arabidopsis

<400> SEQUENCE: 5
gtgggctaaa aagggtgacg aagaagaaag aagagtgacc tctctctcgc atatttttct     60
ttccgatata tatatctttt ataatatttg tgaattctga ataaactctt agtaagaaag    120
aaaaggagag tccagaaaaa gaaagcgaga agagagaga gaaaacgata cctaagctca    180
attatcttct ctgcaacaaa ctccaaaggt attatcttct tatgctctct ctttgcatac    240
atacatatat atagatacct acatatatat atctctatgt ctttgttcat catcagttat    300
ataggtgatg tagatagatg gacaaaaaaa cagcgtaaga cctagtttct gacttacata    360
tgttttaaat tctttgtctg aatcattaca ggatccgaga gagagagctc tggaacgata    420
ttaacatata tcatgaagaa aaagattgaa gtattgatg gggataaact aaaacttctc    480
```

```
ctaatactac aattctcttg aagacttttc acaataattc tatgtcccaa gattatcatc    540
atcatcatca tcataatcaa caccaaggag gtatcttcaa cttctctaat ggattcgacc    600
gatcagattc tcccaattta acaactcagc agaagcaaga gcatcaaagg gtagagatgg    660
acgaggaatc ttcagtcgcc ggaggtagga ttccggtcta cgaatcagcc ggtatgttat    720
ccgaaatgtt taatttcccc ggaagcagcg gtggaggaag agatctcgac ctcggccaat    780 cttccggtc aaataggcag ttgcttgagg agcaacatca gaatattccg gctatgaatg    840
ctacggattc agccaccgcc accgcagccg ccatgcagtt attcttgatg aatccaccgc    900
caccgcaaca accaccgtct ccgtcatcca caacttcccc aaggagccac cacaattctt    960
caactcttca catgttactt ccaagtccat ccaccaacac aactcaccat cagaactaca   1020
ctaatcatat gtctatgcat cagcttccac atcagcatca ccagcagata tcgacgtggc   1080
agtcttctcc cgatcatcat catcatcatc acaacagcca aacggagatt gggaccgtcc   1140
acgtggaaaa cagcggagga cacggaggac aaggcttgtc cttatctctc tcatcgtctt   1200
tagaggctgc agcaaaagcg gaagagtata gaaacattta ctacgagcc aattcttcta   1260 acgcatcacc tcatcatcaa tacaatcaat tcaagactct tcttgctaat tcttctcaac   1320
atcaccatca agtattaaac caattccgat catctccggc tgcttcttcc tcttccatgg   1380
cagcggtcaa tatcttaaga aactcgaggt acacaacggc cgcgcaagag ttgttggaag   1440
agttttgtag tgttggaaga ggattttttga agaagaacaa acttgggaac agctcaaacc   1500
ctaatacttg cggtggtgat ggtggtggca gctctccttc gtcggccgga gcaaacaagg   1560
agcatcctcc tttatcggcg tctgatcgga ttgagcatca aagaaggaaa gtgaaactac   1620
tcaccatgct tgaagaggta tgttcatatt aacttttaat attgattttg actttgtcta   1680
tactctacag tgatattagt tcatacattt tacgtaaaat tgttttcgtt acatttcgat   1740
aagattcata aattgatcca agagttatga caaagaaaca agaaacctga tatgactgaa   1800
ttggtctttt gttttctcga ttaactactt attttttgatt attttggtag agtttgattg   1860
cgcaatccta ccatcatttg tttaaaatta aaattaatttt aatcattttg ctcgtgtgac   1920
ggtcgtatta gaaagtatat tgaatatttt gatgcttagc gtttggtgga atcgattaat   1980
caaagaaaat gcattaaata attacgatta attatgtaat tggcgttttcc ttctccatat   2040 aagctactct ccagttacgt cctaaagcta acccttgacg ttacttattt gtttacccat   2100
aattgaatta tctactttt agttgacctt gcttttttct cactagaaat aaatatttta   2160
gtttatgctc gaggatacga taaaatgtgc tgttggtagg attgcgcaaa cattgaagta   2220
tattctctgg tcaataattt gtctatataa tatcttattt tcttattttg tctcgtttaa   2280
aggtaactaa ttaatctcat tagtttattt attagatgat gctcgtacac aagcataggt   2340
tcccgtgata aaatctacac taaataataa tcacgtgaac atataacaca acacacacga   2400
gttaacaata acattaatta aaagaaaaag gcaaatattg atatttatgg attgtataat   2460
gtatagtttt gtttcgttgg caggtggacc gacggtacaa ccattactgc gagcaaatgc   2520
agatggttgt gaactctttc gacatagtaa tgggccacgg tgcggcatta ccgtacaccg   2580
cattggctca aaaagctatg tcaagacatt ttagatgcct taaagatgca gttgcggctc   2640
agcttaagca gagttgcgaa cttcttgggg acaaagatgc agcgggaatc tcttcttccg   2700
ggttaacaaa aggtgaaact ccgcgtttgc gtttgctaga gcaaagtttg cgtcagaacc   2760
gtgcgtttca tcaaatgggt atgatggaac aagaagcttg gcggcacaa cgcggtttgc   2820 ctgaacgctc cgtcaatata cttagagctt ggctcttcga acatttcctt cacccgtaag   2880
```

| | | | |
|---|---|---|---|
| tcaatttttt | ctttctttct | cgttatttat | taattattat agagaaactg aattttgaaa | 2940 |
| aaagctgaga | aaaagtattt | attttctcgt | tatttcacct ctactttctt tagtactatg | 3000 |
| tctctagaat | tttgctattt | tattgttaac | gagagtgaac gaaaaaatgg aaataaagca | 3060 |
| aaagagtagt | gttttgtac | tattttcacc | tctctgacaa attgctttaa gagtaaaaca | 3120 |
| aaacaaaaaa | agccaagtaa | aaaaaaaaaa | actggatcga tgatatgtaa tcatcaactt | 3180 |
| ttcttttgtc | tgttagattc | tcacgcccctt | gttaggaaaa agtctgtact ttttcttgcg | 3240 |
| tctacttgat | tgtattgtat | atagtgaaaa | gataagaaaa ataaattaca ttgagtttat | 3300 |
| tagggcaaag | atagagagtg | atgtcatttt | ctggtctctt tctcaggtat ccaagtgatg | 3360 |
| cagataaaca | cctattggct | cgacagactg | gtttatccag aaatcaggtc agtctacata | 3420 |
| tatacatata | gccaacgata | taatgaaatt | taaaatctcc atgaatcaaa tacatatgcc | 3480 |
| tctacttcac | caagttgtgt | tagctgagta | tactcttaat cagacaatca aatgaccaca | 3540 |
| gtctggatta | cgaattctta | accgcgtgtt | ttaaagattt gttttaaacc catcattcta | 3600 |
| tgtttataaa | taaactccac | aatagtacac | agttatatat ataactacaa tattaattta | 3660 |
| tcacccaaac | ccatttcata | attttcataa | acatatacat gcttgttata aacatcaaat | 3720 |
| aataaatact | agtagttact | caaaacgaat | ttgactaagc caaaattatt tgacaccatg | 3780 |
| tacgagtaca | ctaactagta | gcctgagatg | actctattgc atggttttg tttcttatct | 3840 |
| ttgtttggtt | tgtgatatga | cagaggaaca | ccatgtgttt tgccttccac tcaccattag | 3900 |
| cttttcttgg | gattcgtctt | taaattatta | tagcatattt atatatacaa aaacatagga | 3960 |
| gagagagaaa | gagatcgaca | ttaaagacgc | aaaagggtcc atttttcctc aagtacatca | 4020 |
| aagtttgcag | ctttcaattg | tcccaaagaa | accctcaatt tcttgtatcc ctacattaaa | 4080 |
| taaccaaatg | acaaataaac | aaaaagagcc | ctcaatttta tttcgatatt ataatgattc | 4140 |
| aactagtgaa | aattttgtct | cttttattca | ggtatcaaat tggttcataa atgctagggt | 4200 |
| tcgtttatgg | aaaccaatgg | tggaagaaat | gtaccaacaa gaatcaaaag aaagagaaag | 4260 |
| agaagaggaa | ttagaagaga | acgaagaaga | tcaagaaaca aaaaacagca acgacgacaa | 4320 |
| gagcacaaaa | tccaacaaca | atgaaagcaa | cttcactgcc gttcggacca cttcacaaac | 4380 |
| tccaacgaca | accgcaccag | acgcatcaga | cgcagacgca gcagtagcga caggccaccg | 4440 |
| tctaagatcc | aacattaatg | cttacgaaaa | cgacgcttca tcacttctac tcccttcctc | 4500 |
| ttattccaac | gccgccgctc | ctgccgctgt | ttctgacgac ttgaattctc gttacggtgg | 4560 |
| ctcagacgcg | ttttccgccg | ttgccacgtg | tcaacaaagt gtaggtgggt tcgatgatgc | 4620 |
| tgacatggat | ggtgttaacg | ttataaggtt | tgggacaaac cctactggtg acgtgtctct | 4680 |
| cacgcttggt | ttacgccacg | ctggaaacat | gcctgacaaa gacgcttctt tctgcgttag | 4740 |
| agagtttggg | ggttttagt | ttgctttgt | cactccattt aattaattaa ttatagtttc | 4800 |
| cattcttact | tattttaatt | gaaaatctat | ttttgtctct taaaagtcaa aacaatacat | 4860 |
| tagtctagcc | ctcctctgct | ttttttttc | tatctcgtga agagaagaaa acgatacgta | 4920 |
| aatccccttcg | aaaactaatg | tacgttgtac | gacttattgt tttcat | 4966 |

<210> SEQ ID NO 6
<211> LENGTH: 739
<212> TYPE: PRT
<213> ORGANISM: Arabidopsis

<400> SEQUENCE: 6

-continued

```
Met Gly Ile Thr Lys Thr Ser Pro Asn Thr Ile Leu Leu Lys Thr
1               5                   10                  15

Phe His Asn Asn Ser Met Ser Gln Asp Tyr His His His His His
            20                  25                  30

Asn Gln His Gln Gly Gly Ile Phe Asn Phe Ser Asn Gly Phe Asp Arg
        35                  40                  45

Ser Asp Ser Pro Asn Leu Thr Thr Gln Gln Lys Gln Glu His Gln Arg
    50                  55                  60

Val Glu Met Asp Glu Glu Ser Ser Val Ala Gly Gly Arg Ile Pro Val
65                  70                  75                  80

Tyr Glu Ser Ala Gly Met Leu Ser Glu Met Phe Asn Phe Pro Gly Ser
                85                  90                  95

Ser Gly Gly Gly Arg Asp Leu Asp Leu Gly Gln Ser Phe Arg Ser Asn
            100                 105                 110

Arg Gln Leu Leu Glu Glu Gln His Gln Asn Ile Pro Ala Met Asn Ala
        115                 120                 125

Thr Asp Ser Ala Thr Ala Thr Ala Ala Met Gln Leu Phe Leu Met
    130                 135                 140

Asn Pro Pro Pro Gln Gln Pro Pro Ser Pro Ser Ser Thr Thr Ser
145                 150                 155                 160

Pro Arg Ser His His Asn Ser Ser Thr Leu His Met Leu Leu Pro Ser
                165                 170                 175

Pro Ser Thr Asn Thr Thr His His Gln Asn Tyr Thr Asn His Met Ser
            180                 185                 190

Met His Gln Leu Pro His Gln His His Gln Gln Ile Ser Thr Trp Gln
        195                 200                 205

Ser Ser Pro Asp His His His His His Asn Ser Gln Thr Glu Ile
210                 215                 220

Gly Thr Val His Val Glu Asn Ser Gly Gly His Gly Gly Gln Gly Leu
225                 230                 235                 240

Ser Leu Ser Leu Ser Ser Ser Leu Glu Ala Ala Ala Lys Ala Glu Glu
                245                 250                 255

Tyr Arg Asn Ile Tyr Tyr Gly Ala Asn Ser Ser Asn Ala Ser Pro His
            260                 265                 270

His Gln Tyr Asn Gln Phe Lys Thr Leu Leu Ala Asn Ser Ser Gln His
        275                 280                 285

His His Gln Val Leu Asn Gln Phe Arg Ser Ser Pro Ala Ala Ser Ser
    290                 295                 300

Ser Ser Met Ala Ala Val Asn Ile Leu Arg Asn Ser Arg Tyr Thr Thr
305                 310                 315                 320

Ala Ala Gln Glu Leu Leu Glu Glu Phe Cys Ser Val Gly Arg Gly Phe
                325                 330                 335

Leu Lys Lys Asn Lys Leu Gly Asn Ser Ser Asn Pro Asn Thr Cys Gly
            340                 345                 350

Gly Asp Gly Gly Ser Ser Pro Ser Ala Gly Ala Asn Lys Glu
        355                 360                 365

His Pro Pro Leu Ser Ala Ser Asp Arg Ile Glu His Gln Arg Arg Lys
    370                 375                 380

Val Lys Leu Leu Thr Met Leu Glu Glu Val Asp Arg Arg Tyr Asn His
385                 390                 395                 400

Tyr Cys Glu Gln Met Gln Met Val Val Asn Ser Phe Asp Ile Val Met
                405                 410                 415

Gly His Gly Ala Ala Leu Pro Tyr Thr Ala Leu Ala Gln Lys Ala Met
```

```
                        420                 425                 430
Ser Arg His Phe Arg Cys Leu Lys Asp Ala Val Ala Ala Gln Leu Lys
            435                 440                 445

Gln Ser Cys Glu Leu Leu Gly Asp Lys Asp Ala Ala Gly Ile Ser Ser
        450                 455                 460

Ser Gly Leu Thr Lys Gly Glu Thr Pro Arg Leu Arg Leu Leu Glu Gln
465                 470                 475                 480

Ser Leu Arg Gln Asn Arg Ala Phe His Gln Met Gly Met Met Glu Gln
                485                 490                 495

Glu Ala Trp Arg Pro Gln Arg Gly Leu Pro Glu Arg Ser Val Asn Ile
            500                 505                 510

Leu Arg Ala Trp Leu Phe Glu His Phe Leu His Pro Tyr Pro Ser Asp
            515                 520                 525

Ala Asp Lys His Leu Leu Ala Arg Gln Thr Gly Leu Ser Arg Asn Gln
        530                 535                 540

Val Ser Asn Trp Phe Ile Asn Ala Arg Val Arg Leu Trp Lys Pro Met
545                 550                 555                 560

Val Glu Glu Met Tyr Gln Gln Glu Ser Lys Glu Arg Glu Arg Glu Glu
                565                 570                 575

Glu Leu Glu Glu Asn Glu Glu Asp Gln Glu Thr Lys Asn Ser Asn Asp
            580                 585                 590

Asp Lys Ser Thr Lys Ser Asn Asn Glu Ser Asn Phe Thr Ala Val
        595                 600                 605

Arg Thr Thr Ser Gln Thr Pro Thr Thr Thr Ala Pro Asp Ala Ser Asp
        610                 615                 620

Ala Asp Ala Ala Val Ala Thr Gly His Arg Leu Arg Ser Asn Ile Asn
625                 630                 635                 640

Ala Tyr Glu Asn Asp Ala Ser Ser Leu Leu Leu Pro Ser Ser Tyr Ser
                645                 650                 655

Asn Ala Ala Ala Pro Ala Ala Val Ser Asp Asp Leu Asn Ser Arg Tyr
            660                 665                 670

Gly Gly Ser Asp Ala Phe Ser Ala Val Ala Thr Cys Gln Gln Ser Val
        675                 680                 685

Gly Gly Phe Asp Asp Ala Asp Met Asp Gly Val Asn Val Ile Arg Phe
        690                 695                 700

Gly Thr Asn Pro Thr Gly Asp Val Ser Leu Thr Leu Gly Leu Arg His
705                 710                 715                 720

Ala Gly Asn Met Pro Asp Lys Asp Ala Ser Phe Cys Val Arg Glu Phe
                725                 730                 735

Gly Gly Phe
```

ARABIDOPSIS NONHOST RESISTANCE GENE(S) AND USE THEREOF TO ENGINEER SDS RESISTANT PLANTS

CROSS-REFERENCED TO RELATED APPLICATIONS

This application claims priority under 35 U.S.C § 119 to provisional application Ser. No. 62/100,306 filed Jan. 6, 2015, herein incorporated by reference in its entirety.

GRANT REFERENCE

This invention was made with government support under Grant No. 2013-68004-20374 awarded by USDA/NIFA. The government has certain rights in the invention.

FIELD OF THE INVENTION

The present invention is in the field of plant genetics. More specifically, the invention relates to nucleic acid molecules from regions of the *Arabidopsis* genome which are associated with nonhost pathogen resistance, particularly to *Phytophthora* spp. and *Fusarium virguliforme*. The invention also relates to proteins encoded by such nucleic acid molecules as well as nucleic acid markers which are associated with *Fusarium* resistance. Moreover, the invention relates to uses of such molecules, including, transforming *Fusarium* and *Phytophthora* susceptible plants with constructs containing the nucleic acid molecules to create transgenic plants with *Fusarium* and *Phytophthora* resistance and the use of such molecules, transformed cells, plants and plant parts in a plant breeding program.

BACKGROUND OF THE INVENTION

Soybean [*Glycine max* L. (Merrill)] is a major oil seed crop and is grown throughout much of the world. The United States alone produces over half of the world output. Soybean seed typically contains 40% protein and 20% oil and is used primarily for livestock feed and industrial purposes, in addition to human consumption. Soybeans are a major cash crop and investment commodity in North America and elsewhere. Soybean oil is one of the most widely used edible oils, and soybeans are used worldwide both in animal feed and in human food production.

Soybean sudden death syndrome (SDS) is a fungal disease of soybean (*Glycine max* (L.)), caused by *Fusarium solani*. Since its discovery SDS has become one of the most destructive pests in soybean. It has been reported in nearly all states that soybean are grown, and it causes production problems in several states, being particularly destructive in Midwestern states. See generally (Mulrooney 1988, Gibson et al., 1994, Hartman et al., 1995, Wrather et al., 1995, 1996). Nationwide, the estimated soybean yield suppression from SDS in 2010 was 2.1% of total yield valued at $0.82 billion. In certain years, SDS causes total crop loss in many soybean fields.

Although the use of fungicides is effective in reducing the population level of the fungus, fungicide use is both uneconomical and environmentally unsound as a control measure in soybean production. Neither is crop rotation a practical means of fungal control since rotation with a non-susceptible crop for at least two years is necessary for reducing soybean losses. Therefore, soybean breeders generally rely on the use of resistant varieties as the most practical control measure.

Resistance generally means the ability of a plant to prevent, or at least curtail the infestation and colonization by a harmful pathogen. Different mechanisms can be discerned in the naturally occurring resistance, with which the plants fend off colonization by phytopathogenic organisms. These specific interactions between the pathogen and the host determine the course of infection (Schopfer and Brennicke (1999) Pflanzenphysiologie, Springer Verlag, Berlin-Heidelberg, Germany).

Resistance to SDS is multigenic and quantitative in soybean (Hnetkovsky et al., 1996; Njiti et al., 1996). Chang et al., (1996, 1997) estimated that Forrest has 5 genes required for resistance to SDS. Njiti et al., (1996) and Kilo et al., (1996) estimated that Pyramid has genes required for resistance to SDS, 2 that were different from those in Forrest. The multiple genes and genetic backgrounds involved contribute to the difficulty breeders have in developing SDS resistant soybean varieties.

With regard to race specific resistance, also called host resistance, a differentiation is made between compatible and incompatible interactions. In the compatible interaction, an interaction occurs between a virulent pathogen and a susceptible plant. The pathogen survives, and may build up reproduction structures, while the host dies off. An incompatible interaction occurs on the other hand when the pathogen infects the plant but is inhibited in its growth before or after weak development of symptoms. In the latter case, the plant is resistant to the respective pathogen (Schopfer and Brennick, vide supra). In both compatible and incompatible interactions a defensive and specific reaction of the host to the pathogen occurs.

In nature, however, this host resistance is often overcome because of the rapid evolutionary development of pathogens (Neu et al. (2003) American Cytopathol. Society, MPMI 16 No. 7: 626-633). In contrast, non-host resistance offers strong, broad, and permanent protection from phytopathogens. Non-host resistance relates to the phenomenon where a pathogen can induce a disease in a certain plant species, but not in other plant species (Heath (2002) Can. J. Plant Pathol. 24: 259-264).

Despite this interesting characteristic, the genetic and molecular biological basis for nonhost resistance have up to now only been poorly understood. There are indications that non-host resistance is induced by unspecific agents, and also that individual pathogen proteins induce the non-host resistance reaction (Heath (1981) Phytopathology 71: 1121-1123; Heath (2001) Physiol. Mol. Plant. Pathol. 58: 53-54; Kamoun et al. (1998) Plant Cell 10: 1413-1425; Lauge et al. (2000) Plant J. 23: 735-745; Whalen et al. (1988) Proc. Natl. Acad. Sci. USA 85: 6743-6747). The phenomenon of non-host resistance might also be based on structural or chemical properties of the plant species, such as the thickness of the cuticle or the presence of inhibitory substances.

It is an object of the present invention to use non-host resistance in *Arabidopsis* to engineer resistance to susceptible host plants against *Phytophthora* and particuarlly, *Fusarium*.

Other objects will become apparent from the description of the invention which follows.

SUMMARY OF THE INVENTION

In one aspect, this invention relates to nucleic acid isolated from *Arabidopsis thaliana* which are associated with its non-host resistance to *Fusarium*. Also according to the invention, protein sequences are disclosed which are encoded by the same. These sequences alone, or in combination with other sequences, can be used to improve the resistance in susceptible plant species such as soybean to *Fusarium*. In another aspect of the present invention, expression cassettes and transformation vectors comprising the isolated nucleotide sequences are disclosed. The transformation vectors can be used to transform plants and express these pathogen non host resistance genes in the transformed cells. Transformed cells as well as regenerated transgenic plants and seeds containing and expressing the isolated DNA sequences and protein products are also provided. Therefore, in one aspect, the present invention relates to an isolated nucleic acid comprising an isolated polynucleotide sequence encoding a non-host resistance gene product isolated from *Arabidopsis* that confers its non-host resistance. Several non-host resistance genes have been identified according to the invention, including pss 6-At4g15780 (vesicle-associated membrane protein 724) (SEQ ID NOS: 1 and 2); pss 21-At5g64940 (oxidative stress-related abc1-like protein 1) (SEQ ID NOS: 3 and 4) and pss 25 At4g36870 (BLH2-BEL1-like homeodomain protein 2) (SEQ ID NOS 5 and 6). Sequences reported above are non-limiting examples of potential coding sequences of these genes recited herein and are reported as CDS, amino acid, and genomic respectively.

In a further aspect, the present invention includes a nucleic acid selected from: (a) an isolated polynucleotide encoding a polypeptide of the present invention; (b) a polynucleotide having at least 90% or 95% identity to a polynucleotide of the present invention; (c) a polynucleotide comprising at least 50 or more nucleotides in length which hybridizes under high stringency conditions to a polynucleotide of the present invention; (d) a polynucleotide comprising a polynucleotide of the present invention; and (e) a polynucleotide which is complementary to the polynucleotide of (a) to (e). The present invention includes and provides a method of investigating a haplotype of a plant comprising: (A) isolating nucleic acid molecules from the plant; (B) determining the nucleic acid sequence of a non-host resistance gene; and, (C) comparing the nucleic acid sequence of the allele or part thereof to a reference nucleic acid sequence. The present invention includes and provides a method of introgressing *Fusarium* resistance or partial *Fusarium* resistance into a susceptible plant comprising: performing marker assisted selection of the plant with a nucleic acid marker, wherein the nucleic acid marker specifically hybridizes with a nucleic acid molecule encoding a nonhost resistance gene reported herein and, selecting the plant based on the marker assisted selection.

The present invention includes and provides a method of investigating a nonhost *Phytophtora* and *Fusarium* resistance haplotype of a plant comprising: (A) isolating nucleic acid molecules from the plant; (B) determining the nucleic acid sequence of an nonhost resistance allele or part thereof; and (C) comparing the nucleic acid sequence of the allele or part thereof to a reference nucleic acid sequence.

In another aspect, the present invention relates to a recombinant expression cassette comprising a nucleic acid as described, supra. Additionally, the present invention relates to a vector containing the recombinant expression cassette. Further, the vector containing the recombinant expression cassette can facilitate the transcription and translation of the nucleic acid in a host cell. The present invention also relates to host cells able to express the polynucleotide of the present invention. A number of host cells could be used, such as but not limited to, microbial, mammalian, plant, or insect. Thus the invention is also directed to transgenic cells, containing the nucleic acids of the present invention as well as cells, plants, tissue cultures and ultimately lines derived therefrom. The invention also relates to vectors and cassettes designed to introduce the expression of nonhost resistance proteins for modulation of the *Fusarium* interaction, or for delineation of information about the regulatory pathways involving the same.

This invention also provides an isolated polypeptide comprising (a) a polypeptide comprising at least 90% or 95% sequence identity to a polypeptide of the present invention (b) a polypeptide encoded by a nucleic acid of the present invention; and (c) a polypeptide comprising a nonhost resistance activity and comprising conserved structural domain motifs of the same.

Another embodiment of the subject invention comprises methods for engineering broad-spectrum pathogen resistance in soybean or other *Fusarium* susceptible crop plants by introducing nonhost resistance protein encoding sequences to said plants. Plants' tolerance to *Fusarium* and other soybean pathogens may be improved by elucidating the pathways that regulate gene transcription involved in enhancing accumulation of products shown to be associated with expression of other pathogen resistance, methods for providing for increased nonspecific resistance to particularly virulent races or strains of pathogenic agents including *P. sojae*, *Pseudomonas syringae* pv. *glycenia* (Psg), soybean cyst nematode (SCN), *Fusarium virguliforme* or soybean mosaic virus.

Nucleotide sequences isolated from the nonhost resistance genes which may be introduced to plants can be used in developing perfect molecular markers that can be routinely used in breeding programs for incorporating *Fusarium* resistance into new cultivars.

Units, prefixes, and symbols may be denoted in their SI accepted form. Unless otherwise indicated, nucleic acids are written left to right in 5' to 3' orientation; amino acid sequences are written left to right in amino to carboxy orientation, respectively. Numeric ranges are inclusive of the numbers defining the range and include each integer within the defined range. Amino acids may be referred to herein by either their commonly known three letter symbols or by the one-letter symbols recommended by the IUPAC-IUB Biochemical nomenclature Commission. Nucleotides, likewise, may be referred to by their commonly accepted single-letter codes. Unless otherwise provided for, software, electrical, and electronics terms as used herein are as defined in The New IEEE Standard Dictionary of Electrical and Electronics Terms (5$^{th}$ edition, 1993). The terms defined below are more fully defined by reference to the specification as a whole.

By "amplified" is meant the construction of multiple copies of a nucleic acid sequence or multiple copies complementary to the nucleic acid sequence using at least one of the nucleic acid sequences as a template. Amplification systems include the polymerase chain reaction (PCR) system, ligase chain reaction (LCR) system, nucleic acid sequence based amplification (NASBA, Canteen, Mississauga, Ontario), Q-Beta Replicase systems, transcription-based amplification system (TAS), and strand displacement amplification (SDA). See, e.g., *Diagnostic Molecular Microbiology: Principles and Applications*, D. H. Persing et al., Ed., American Society for Microbiology, Washington, D.C. (1993). The product of amplification is termed an amplicon.

As used herein, "chromosomal region" includes reference to a length of a chromosome that may be measured by reference to the linear segment of DNA that it comprises. The chromosomal region can be defined by reference to two unique DNA sequences, i.e., markers.

The term "conservatively modified variants" applies to both amino acid and nucleic acid sequences. With respect to particular nucleic acid sequences, conservatively modified variants refer to those nucleic acids which encode identical or conservatively modified variants of the amino acid sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation. Every nucleic acid sequence herein that encodes a polypeptide also, by reference to the genetic code, describes every possible silent variation of the nucleic acid. One of ordinary skill will recognize that each codon in a nucleic acid (except AUG, which is ordinarily the only codon for methionine; and UGG, which is ordinarily the only codon for tryptophan) can be modified to yield a functionally identical molecule. Accordingly, each silent variation of a nucleic acid which encodes a polypeptide of the present invention is implicit in each described polypeptide sequence and is within the scope of the present invention.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Thus, any number of amino acid residues selected from the group of integers consisting of from 1 to 15 can be so altered. Thus, for example, 1, 2, 3, 4, 5, 7, or 10 alterations can be made. Conservatively modified variants typically provide similar biological activity as the unmodified polypeptide sequence from which they are derived. For example, substrate specificity, enzyme activity, or ligand/receptor binding is generally at least 30%, 40%, 50%, 60%, 70%, 80%, or 90% of the native protein for its native substrate. Conservative substitution tables providing functionally similar amino acids are well known in the art.

The following six groups each contain amino acids that are conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).
See also, Creighton (1984) Proteins W.H. Freeman and Company.

By "encoding" or "encoded", with respect to a specified nucleic acid, is meant comprising the information for translation into the specified protein. A nucleic acid encoding a protein may comprise non-translated sequences (e.g., introns) within translated regions of the nucleic acid, or may lack such intervening non-translated sequences (e.g., as in cDNA). The information by which a protein is encoded is specified by the use of codons. Typically, the amino acid sequence is encoded by the nucleic acid using the "universal" genetic code. However, variants of the universal code, such as are present in some plant, animal, and fungal mitochondria, the bacterium *Mycoplasma capricolum*, or the ciliate *Macronucleus*, may be used when the nucleic acid is expressed therein.

When the nucleic acid is prepared or altered synthetically, advantage can be taken of known codon preferences of the intended host where the nucleic acid is to be expressed. For example, although nucleic acid sequences of the present invention may be expressed in both monocotyledonous and dicotyledonous plant species, sequences can be modified to account for the specific codon preferences and GC content preferences of monocotyledons or dicotyledons as these preferences have been shown to differ (Murray et al. *Nucl. Acids Res.* 17:477-498 (1989)).

As used herein "full-length sequence" in reference to a specified polynucleotide or its encoded protein means having the entire amino acid sequence of, a native (non-synthetic), endogenous, biologically active form of the specified protein. Methods to determine whether a sequence is full-length are well known in the art including such exemplary techniques as northern or western blots, primer extensions, S1 protection, and ribonuclease protection. See, e.g., *Plant Molecular Biology: A Laboratory Manual*, Clark, Ed., Springer-Verlag, Berlin (1997). Comparison to known full-length homologous (orthologous and/or paralogous) sequences can also be used to identify full-length sequences of the present invention. Additionally, consensus sequences typically present at the 5' and 3' untranslated regions of mRNA aid in the identification of a polynucleotide as full-length. For example, the consensus sequence ANNNN <u>AUG</u>G, where the underlined codon represents the N-terminal methionine, aids in determining whether the polynucleotide has a complete 5' end. Consensus sequences at the 3' end, such as polyadenylation sequences, aid in determining whether the polynucleotide has a complete 3' end.

As used herein, "heterologous" in reference to a nucleic acid is a nucleic acid that originates from a foreign species, or, if from the same species, is substantially modified from its native form in composition and/or genomic locus by deliberate human intervention. For example, a promoter operably linked to a heterologous structural gene is from a species different from that from which the structural gene was derived, or, if from the same species, one or both are substantially modified from their original form. A heterologous protein may originate from a foreign species or, if from the same species, is substantially modified from its original form by deliberate human intervention.

By "host cell" is meant a cell which contains a vector and supports the replication and/or expression of the vector. Host cells may be prokaryotic cells such as *E. coli*, or eukaryotic cells such as yeast, insect, amphibian, or mammalian cells. Preferably, host cells are monocotyledonous or dicotyledonous plant cells. A particularly preferred monocotyledonous host cell is a maize host cell.

The term "hybridization complex" includes reference to a duplex nucleic acid structure formed by two single-stranded nucleic acid sequences selectively hybridized with each other.

The term "introduced" in the context of inserting a nucleic acid into a cell, means "transfection" or "transformation" or "transduction" and includes reference to the incorporation of a nucleic acid into a eukaryotic or prokaryotic cell where the nucleic acid may be incorporated into the genome of the cell (e.g., chromosome, plasmid, plastid or mitochondrial DNA), converted into an autonomous replicon, or transiently expressed (e.g., transfected mRNA).

The term "isolated" refers to material, such as a nucleic acid or a protein, which is: (1) substantially or essentially free from components that normally accompany or interact with it as found in its naturally occurring environment. The isolated material optionally comprises material not found with the material in its natural environment; or (2) if the material is in its natural environment, the material has been synthetically (non-naturally) altered by deliberate human intervention to a composition and/or placed at a location in the cell (e.g., genome or subcellular organelle) not native to a material found in that environment. The alteration to yield the synthetic material can be performed on the material within or removed from its natural state. For example, a naturally occurring nucleic acid becomes an isolated nucleic acid if it is altered, or if it is transcribed from DNA which has been altered, by means of human intervention performed within the cell from which it originates. See, e.g., Compounds and Methods for Site Directed Mutagenesis in Eukaryotic Cells, Kmiec, U.S. Pat. No. 5,565,350; In Vivo Homologous Sequence Targeting in Eukaryotic Cells; Zarling et al., PCT/US93/03868. Likewise, a naturally occurring nucleic acid (e.g., a promoter) becomes isolated if it is introduced by non-naturally occurring means to a locus of the genome not native to that nucleic acid. Nucleic acids which are "isolated" as defined herein, are also referred to as "heterologous" nucleic acids.

As used herein, "localized within the chromosomal region defined by and including" with respect to particular markers includes reference to a contiguous length of a chromosome delimited by and including the stated markers.

As used herein, "marker" includes reference to a locus on a chromosome that serves to identify a unique position on the chromosome. A "polymorphic marker" includes reference to a marker which appears in multiple forms (alleles) such that different forms of the marker, when they are present in a homologous pair, allow transmission of each of the chromosomes of that pair to be followed. A genotype may be defined by use of one or a plurality of markers.

As used herein, the term "nonhost resistance protein" shall include any amino acid sequence which retain one or more of the properties of proteins listed herein in general. They also must be capable of interacting with *Fusarium* infection in that loss of function mutations can render an *Arabidopsis* plant susceptible to *Fusarium* infection. Such proteins may include Pss6-At4g15780 (vesicle-associated membrane protein 724) (SEQ ID NOS: 1 and 2); Pss21-At5g64940 (oxidative stress-related abc1-like protein 1)(SEQ ID NOS: 3 and 4) and Pss25 At4g36870 (BLH2-BEL1-like homeodomain protein 2) (SEQ ID NOS 5 and 6) and any conservatively modified variants, fragments, and homologs or full length sequences incorporating the same which retain the *Phyphthora* infection related activity described herein. Nonhost resistance proteins are capable of suppressing, controlling, and/or preventing invasion by the pathogenic organism. A non host resistance protein will reduce the disease symptoms resulting from pathogen challenge in a previously susceptible plant by at least about 2%, including but not limited to, about 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, or greater. In particular embodiments, the disease symptoms resulting from pathogen challenge are reduced by non host resistance protein by at least about 5% to about 50%, at least about 10% to about 60%, at least about 30% to about 70%, at least about 40% to about 80%, or at least about 50% to about 90% or greater. Hence, the methods of the invention can be utilized to protect plants from disease, particularly those diseases that are caused by plant pathogens. Resistance may vary from a slight increase in tolerance to the effects of the pathogen (e.g., partial inhibition) to total resistance such that the plant is unaffected by the presence of the pathogen. An increased level of resistance against a particular pathogen or against a wider spectrum of pathogens may both constitute complete resistance or improved resistance.

"Pathogen resistance", "disease resistance" or "*Fusarium* resistance" is intended to mean that the plant avoids the disease symptoms that are the outcome of plant-pathogen interactions. That is, pathogens are prevented from causing plant diseases and the associated disease symptoms, or alternatively, the disease symptoms caused by the pathogen are minimized or lessened, such as, for example, the reduction of stress and associated yield loss.

Assays that measure antipathogenic activity are commonly known in the art, as are methods to quantitate disease resistance in plants following pathogen infection. See, for example, U.S. Pat. No. 5,614,395, herein incorporated by reference. Such techniques include, measuring over time, the average lesion diameter, the pathogen biomass, and the overall percentage of decayed plant tissues. For example, a plant either expressing a nonhost resistance polypeptide shows a decrease in tissue necrosis (i.e., lesion diameter) or a decrease in plant death following pathogen challenge when compared to a control plant that was not engineered to express the nonhost resistance protein.

Alternatively, antipathogenic activity can be measured by a decrease in pathogen biomass. For example, a plant expressing non host resistance protein is challenged with a pathogen of interest. Over time, tissue samples from the pathogen-inoculated tissues are obtained and RNA is extracted. The percent of a specific pathogen RNA transcript relative to the level of a plant specific transcript allows the level of pathogen biomass to be determined. See, for example, Thomma et al. (1998) Plant Biology 95:15107-15111, herein incorporated by reference. According to the invention, the term "increased resistance" (against *Fusarium* sp.) is understood to mean that the transgenic plants, or plant cells, according to the invention are less vigorously, and/or less frequently, affected by *Fusarium* than non-transformed wild type plants, or plant cells, which were otherwise treated in the same way (such as climate and cultivation conditions, pathogen type, etc.). According to the invention, the term "wild type" is to be understood as the respective non-genetically modified parent organism. The penetration efficiency as well as the rate of papillae formation offer a possibility to quantify the reaction of the plant to the pathogen infestation (see examples). The term "increased resistance" also comprises what is known as transient pathogen resistance, i.e. the transgenic plants, or plant cells, according to the invention have an increased pathogen resistance as compared to the respective wild type only for a limited period of time.

By "nucleic acid library" is meant a collection of isolated DNA or cDNA molecules which comprise and substantially represent the entire transcribed fraction of a genome of a specified organism. Construction of exemplary nucleic acid libraries, such as genomic and cDNA libraries, is taught in standard molecular biology references such as Berger and Kimmel, *Guide to Molecular Cloning Techniques, Methods in Enzymology*, Vol. 152, Academic Press, Inc., San Diego, Calif. (Berger); Sambrook et al., *Molecular Cloning—A Laboratory Manual*, $2^{nd}$ ed., Vol. 1-3 (1989); and *Current Protocols in Molecular Biology*, F. M. Ausubel et al., Eds., Current Protocols, a joint venture between Greene Publishing Associates, Inc. and John Wiley & Sons, Inc. (1994).

As used herein "operably linked" includes reference to a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame.

As used herein, the term "plant" can include reference to whole plants, plant parts or organs (e.g., leaves, stems, roots, etc.), plant cells, seeds and progeny of same. Plant cell, as used herein, further includes, without limitation, cells obtained from or found in: seeds, suspension cultures, embryos, meristematic regions, callus tissue, leaves, roots, shoots, gametophytes, sporophytes, pollen, and microspores. Plant cells can also be understood to include modified cells, such as protoplasts, obtained from the aforementioned tissues. The class of plants which can be used in the methods of the invention is generally as broad as the class of higher plants amenable to transformation techniques, including both monocotyledonous and dicotyledonous plants. Particularly preferred plants include maize, soybean, sunflower, sorghum, canola, wheat, alfalfa, cotton, rice, barley, and millet.

As used herein, "polynucleotide" includes reference to a deoxyribopolynucleotide, ribopolynucleotide, or analogs thereof that have the essential nature of a natural ribonucleotide in that they hybridize, under stringent hybridization conditions, to substantially the same nucleotide sequence as naturally occurring nucleotides and/or allow translation into the same amino acid(s) as the naturally occurring nucleotide (s). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons as "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including among other things, simple and complex cells.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein that protein is specifically reactive to antibodies elicited to the same protein but consisting entirely of naturally occurring amino acids. The terms "polypeptide", "peptide" and "protein" are also inclusive of modifications including, but not limited to, glycosylation, lipid attachment, sulfation, gamma-carboxylation of glutamic acid residues, hydroxylation and ADP-ribosylation. It will be appreciated, as is well known and as noted above, that polypeptides are not entirely linear. For instance, polypeptides may be branched as a result of ubiquitination, and they may be circular, with or without branching, generally as a result of posttranslation events, including natural processing event and events brought about by human manipulation which do not occur naturally. Circular, branched and branched circular polypeptides may be synthesized by non-translation natural process and by entirely synthetic methods, as well. Further, this invention contemplates the use of both the methionine-containing and the methionine-less amino terminal variants of the protein of the invention.

As used herein "promoter" includes reference to a region of DNA upstream from the start of transcription and involved in recognition and binding of RNA polymerase and other proteins to initiate transcription. A "plant promoter" is a promoter capable of initiating transcription in plant cells whether or not its origin is a plant cell. Exemplary plant promoters include, but are not limited to, those that are obtained from plants, plant viruses, and bacteria which comprise genes expressed in plant cells such as *Agrobacterium* or *Rhizobium*. Examples of promoters under developmental control include promoters that preferentially initiate transcription in certain tissues, such as leaves, roots, or seeds. Such promoters are referred to as "tissue preferred". Promoters which initiate transcription only in certain tissue are referred to as "tissue specific". A "cell type" specific promoter primarily drives expression in certain cell types in one or more organs, for example, vascular cells in roots or leaves. An "inducible" or "repressible" promoter is a promoter which is under environmental control. Examples of environmental conditions that may affect transcription by inducible promoters include anaerobic conditions or the presence of light. Tissue specific, tissue preferred, cell type specific, and inducible promoters constitute the class of "non-constitutive" promoters. A "constitutive" promoter is a promoter which is active under most environmental conditions.

As used herein "recombinant" includes reference to a cell or vector, that has been modified by the introduction of a heterologous nucleic acid or that the cell is derived from a cell so modified. Thus, for example, recombinant cells express genes that are not found in identical form within the native (non-recombinant) form of the cell or express native genes that are otherwise abnormally expressed, under-expressed or not expressed at all as a result of deliberate human intervention. The term "recombinant" as used herein does not encompass the alteration of the cell or vector by naturally occurring events (e.g., spontaneous mutation, natural transformation/transduction/transposition) such as those occurring without deliberate human intervention.

As used herein, a "recombinant expression cassette" is a nucleic acid construct, generated recombinantly or synthetically, with a series of specified nucleic acid elements which permit transcription of a particular nucleic acid in a host cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid to be transcribed, and a promoter.

The term "residue" or "amino acid residue" or "amino acid" are used interchangeably herein to refer to an amino acid that is incorporated into a protein, polypeptide, or peptide (collectively "protein"). The amino acid may be a naturally occurring amino acid and, unless otherwise limited, may encompass non-natural analogs of natural amino acids that can function in a similar manner as naturally occurring amino acids.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 80% sequence identity, preferably 90% sequence identity, and most preferably 100% sequence identity (i.e., complementary) with each other.

The term "stringent conditions" or "stringent hybridization conditions" includes reference to conditions under which a probe will hybridize to its target sequence, to a detectably greater degree than to other sequences (e.g., at least 2-fold over background). Stringent conditions are sequence-dependent and be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing). Generally, a probe is less than about 1000 nucleotides in length, optionally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 50° C. Exemplary high stringency conditions include hybridization in 50% formamide, 1 M NaCl, 1% SDS at 37° C., and a wash in 0.1×SSC at 60 to 65° C. for 20 minutes.

Specificity is typically the function of post-hybridization washes, the critical factors being the ionic strength and temperature of the final wash solution. For DNA-DNA hybrids, the $T_m$ can be approximated from the equation of Meinkoth and Wahl, *Anal. Biochem.*, 138:267-284 (1984): $T_m$=81.5° C.+16.6 (log M)+0.41 (% GC)–0.61 (% form)–500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of the complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with 90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, *Laboratory Techniques in Biochemistry and Molecular Biology—Hybridization with Nucleic Acids Probes*, Part I, Chapter 2, Ausubel, et al., Eds., Greene Publishing and Wiley-Interscience, New York (1995). In general a high stringency wash is 2×15 min in 0.5×SSC containing 0.1% SDS at 65° C.

As used herein, "transgenic plant" includes reference to a plant which comprises within its genome a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to include any cell, cell line, callus, tissue, plant part or plant, the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

As used herein, "vector" includes reference to a nucleic acid used in transfection of a host cell and into which can be inserted a polynucleotide. Vectors are often replicons. Expression vectors permit transcription of a nucleic acid inserted therein.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" includes reference to a contiguous and specified segment of a polynucleotide sequence, wherein the polynucleotide sequence may be compared to a reference sequence and wherein the portion of the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence, a gap penalty is typically introduced and is subtracted from the number of matches.

Methods of alignment of sequences for comparison are well-known in the art. Optimal alignment of sequences for comparison may be conducted by the local homology algorithm of Smith and Waterman, *Adv. Appl. Math.* 2:482 (1981); by the homology alignment algorithm of Needleman and Wunsch, *J. Mol. Biol.* 48:443 (1970); by the search for similarity method of Pearson and Lipman, *Proc. Natl. Acad. Sci.* 85:2444 (1988); by computerized implementations of these algorithms, including, but not limited to: CLUSTAL in the PC/Gene program by Intelligenetics, Mountain View, Calif.; GAP, BESTFIT, BLAST, FASTA, and TFASTA in the Wisconsin Genetics Software Package, Genetics Computer Group (GCG), 575 Science Dr., Madison, Wis., USA; the CLUSTAL program is well described by Higgins and Sharp, *Gene* 73:237-244 (1988); Higgins and Sharp, *CABIOS* 5:151-153 (1989); Corpet, et al., *Nucleic Acids Research* 16:10881-90 (1988); Huang, et al., *Computer Applications in the Biosciences* 8:155-65 (1992), and Pearson, et al., *Methods in Molecular Biology* 24:307-331 (1994). The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, *Current Protocols in Molecular Biology*, Chapter 19, Ausubel, et al., Eds., Greene Publishing and Wiley-Interscience, New York (1995).

Unless otherwise stated, sequence identity/similarity values provided herein refer to the value obtained using the BLAST 2.0 suite of programs using default parameters. Altschul et al., *Nucleic Acids Res.* 25:3389-3402 (1997). Software for performing BLAST analyses is publicly available, e.g., through the National Center for Biotechnology-Information World Wide Web at ncbi.nih.gov. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) *Proc. Natl. Acad. Sci. USA* 89:10915).

In addition to calculating percent sequence identity, the BLAST algorithm also performs a statistical analysis of the similarity between two sequences (see, e.g., Karlin & Altschul, *Proc. Natl. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance.

BLAST searches assume that proteins can be modeled as random sequences. However, many real proteins comprise regions of nonrandom sequences which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, *Comput. Chem.*, 17:149-163 (1993)) and XNU (Claverie and States, *Comput. Chem.*, 17:191-201 (1993)) low-complexity filters can be employed alone or in combination.

(c) As used herein, "sequence identity" or "identity" in the context of two nucleic acid or polypeptide sequences includes reference to the residues in the two sequences which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Sequences which differ by such conservative substitutions are said to have "sequence similarity" or "similarity". Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, *Computer Applic. Biol. Sci.*, 4:11-17 (1988) e.g., as implemented in the program PC/GENE (Intelligenetics, Mountain View, Calif., USA).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

(e) The term "substantial identity" of polynucleotide sequences means that a polynucleotide comprises a sequence that has at least 70% sequence identity, preferably at least 80%, more preferably at least 90% and most preferably at least 95%, compared to a reference sequence using one of the alignment programs described using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of at least 60%, or preferably at least 70%, 80%, 90%, and most preferably at least 95%.

Another indication that nucleotide sequences are substantially identical is if two molecules hybridize to each other under stringent conditions. However, nucleic acids which do not hybridize to each other under stringent conditions are still substantially identical if the polypeptides which they encode are substantially identical. This may occur, e.g., when a copy of a nucleic acid is created using the maximum codon degeneracy permitted by the genetic code. One indication that two nucleic acid sequences are substantially identical is that the polypeptide which the first nucleic acid encodes is immunologically cross reactive with the polypeptide encoded by the second nucleic acid.

(e) The terms "substantial Identity" in the context of a peptide indicates that a peptide comprises a sequence with at least 70% sequence identity to a reference sequence, preferably 80%, or preferably 85%, most preferably at least 90% or 95% sequence identity to the reference sequence over a specified comparison window. Optionally, optimal alignment is conducted using the homology alignment algorithm of Needleman and Wunsch, *J. Mol. Biol.* 48:443 (1970). An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides which are "substantially similar" share sequences as noted above except that residue positions which are not identical may differ by conservative amino acid changes.

DESCRIPTION OF THE FIGURES

FIG. 1A shows 4 days following inoculation. FIG. 1B shows 7 days following inoculation.

FIG. 2A-2C show the molecular mapping of the Pss21 locus. FIG. 2A shows bulked-segregation analyses of the Pss21 locus: Lane 1, a bulk DNA sample of 14 $F_{2:3}$ susceptible families carrying the Pss21 gene; Lane 2, ecotype Columbia (Col-0), parent of the pss mutants; Lane 3, Niederzenz (Nd-0); and Lane 4, DNA of Col-0 and Nd-0 in equal proportion. Ten $F_{2:3}$ susceptible families carrying mutation in the Pss21 gene were evaluated for molecular markers MBK-5 and LUGSSLP151 (see genetic map positions of these two loci on the south arm of chromosome 5 in C on the right). Note MBK-5 showed only Col-0 phenotype; whereas, LUGSSLP151 showed Nd-0 type. Thus, Pss21 is linked to MBK-5 on south arm of chromosome 5 because pss21 mutant was developed by mutating the progenitor ecoptype, Col-0, and the phenotype of the bulked pss21 pool of 14 families matched the Col-0 phenotype. FIG. 2B shows co-segregation of pss21 with MBK-5 and M555 markers. Ten susceptible $F_{2:3}$ susceptible families carrying the mutant allele, pss1, of the Pss21 gene were evaluated for molecular markers MBK-5 and M555. Note that M555 showed Col-0-type phenotype for all susceptible $F_{2:3}$ families. On the other hand, MBK-5 showed heterozygosity for two susceptible families. Therefore, Pss21 is in between MBK-5 and the telomere and M555 is tightly linked to Pss21. FIG. 2C shows a molecular map of the south arm Chromosome 5 including the Pss21 region (box) is shown.

FIG. 3A shows bulked-segregation analyses of the Pss25 locus: Lane 1, bulked DNA samples of 9 $F_{2:3}$ susceptible families carrying the Pss25 allele; Lane 2, bulked DNA sample of 12 $F_{2:3}$ susceptible families carrying the pss25 allele; Lane 3, a bulk DNA sample of 7 $F_{2:3}$ susceptible families carrying the pss25 allele; Lane 4, ecotype Columbia (Col-0), parent of the pss mutants; Lane 5, Niederzenz (Nd-0); and Lane 6, DNA of Col-0 and Nd in equal proportion. Note that the susceptible bulked DNA samples showed the Col-0 phenotype for SBP5_14.5 and NGA1139 markers; therefore, Pss25 is linked to these two markers. FIG. 3B shows co-segregation of pss25 with SBP4_12.5, SBP4_14.0, NGA1139 and NGA1107 markers. Fifteen $F_{2:3}$ susceptible families carrying mutation in the Pss25 gene were evaluated for molecular markers SBP4_12.5, SBP4_14.0, SBP5_15.06, NGA1139 and NGA1107 (see genetic map positions of these two loci on the south arm of chromosome 4 in FIG. 3C). Note that SBP5_15.06 showed Col-0-type phenotype for all susceptible $F_{2:3}$ families. On the other hand SBP4_12.5, SBP4_14.0, and NGA1107 showed heterozygosity. NGA1139 showed heterozygosity for two susceptible families. Therefore, Pss25 is in between SBP4_15.06 and NGA1139 and SBP4_15.06 is tightly linked to Pss25. Fifteen susceptible $F_{2:3}$ susceptible families carrying the Pss25 gene were evaluated for molecular markers SBP4_12.5, SBP4_14.0, SBP4_15.06, NGA1139 and NGA1137. FIG. 3C shows a molecular map of the south arm chromosome 4 including the Pss25 region (box).

FIG. 4A shows a three-week-old *Arabidopsis* seedlings of Col-0, Nd-0, pen1-1, pss21, T-DNA knock-out lines of candidate Pss21 genes (At5g64940, At5g65380, At5g66020, At5g66350, At5g67150 and At5g64380) were inoculated with *P. sojae* spores at a concentration of $3\times10^5$ spores/ml. Symptoms were evaluated after 48 hour post inoculation. P, T-DNA insertions in promoters; E, T-DNA insertions in exons. FIG. 4B shows confirmation of knock-out of Pss21 gene in T-DNA lines of Pss21 by RT-PCR. RNA was isolated from wild-type (Col-0) and *P. sojae* susceptible T-DNA mutant lines of Pss21 and the expression of Pss21 gene was monitored by RT-PCR. Actin gene is expressed in both Col-0 and Pss21 T-DNA mutant lines (045739, 006766 and 080442) suggesting that Pss1 transcripts are absent in Pss21 T-DNA mutant lines.

FIG. 5A shows three-week-old *Arabidopsis* seedlings of Col-0, Nd-0, pen1-1 and T-DNA knock-out lines (044977, 044886, 063959, 009120, 051518 and 12980) of candidate Pss25 gene (At4g36870) were inoculated with *P. sojae* spores at a concentration of $3\times10^5$ spores/ml. Symptoms were evaluated after 48 hour post inoculation. P, T-DNA insertions in promoters; E, T-DNA insertions in exons and I, T-DNA insertions in exons. FIG. 5B shows confirmation of knockout of Pss25 gene in T-DNA lines of Pss25 by RT-PCR. RNA was isolated from wild-type (Col-0) and *P. sojae* susceptible T-DNA mutant lines of Pss21 and the expression of Pss21 gene was monitored by RT-PCR. Actin gene is expressed in both Col-0 and Pss25 T-DNA mutant lines suggesting that Pss25 transcripts are absent in T-DNA mutant lines.

FIG. 6A shows three-week-old *Arabidopsis* seedlings of Col-0, Nd-0, pen1-1, pss6, T-DNA knock-out lines of candidate Pss6 genes (At4g15130, At4g15780, At4g17100 and At4g16680) were inoculated with *P. sojae* spores at a concentration of $3 \times 10^5$ spores/ml. Symptoms were evaluated after 48 hour post inoculation. E, T-DNA insertions in exons. FIG. 6B shows a molecular characterization of T-DNA insertion pss6 mutants. RNA was isolated from wild-type (Col-0) and *P. sojae* susceptible T-DNA insertion mutant lines and the expression of Pss6 gene (At4g15780) was monitored by RT-PCR. Actin gene is expressed in both Col-0 and Pss6 T-DNA insertion mutant lines (032219 and 011691) However, Pss6-specific transcripts (shown by an arrow) are absent in Pss6 T-DNA mutant lines.

FIG. 7A, FIG. 7B, and FIG. 7E show constructs used for development of transgenic soybean for By "modulating" or "modulation" is intended that the level of expression of a gene may be increased or decreased relative to genes driven by other promoters or relative to the normal or uninduced level of the gene in question.

Figure 1A:
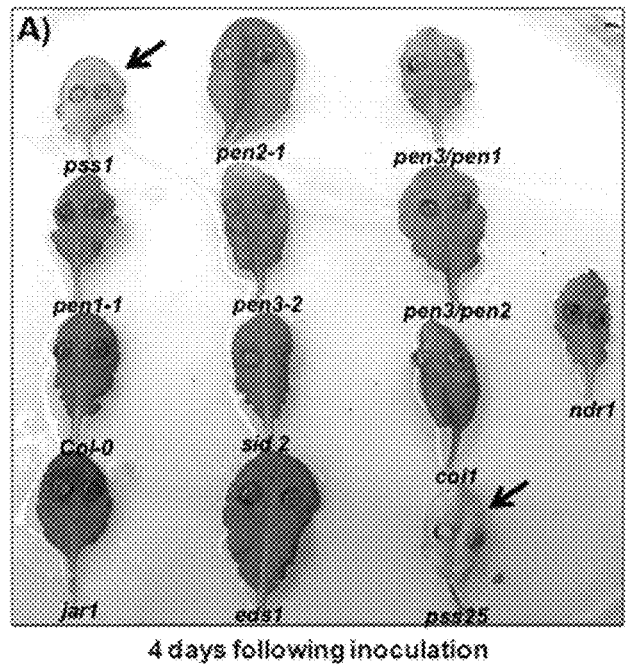
FIGS. 1A-1B are photographs showing that *Arabidopsis* pss1 and pss25 mutants are susceptible to the *Fusarium virguliforme* Mont-1 isolate. Screening of a large mutant *Arabidopsis* population generated by treatment of the germinating seeds of the pen1-1 mutant with the chemical mutagen, ethyl methane sulfonate, resulted in isolation of 30 putative mutants that were susceptible to *Phytophthora sojae*, and were termed as *Phytophthora sojae* susceptible (pss) mutants. pss1, pss21 and pss25 (pss1 and pss25 are shown in the FIGS. 1A-1B with arrows).
Figure 1B:
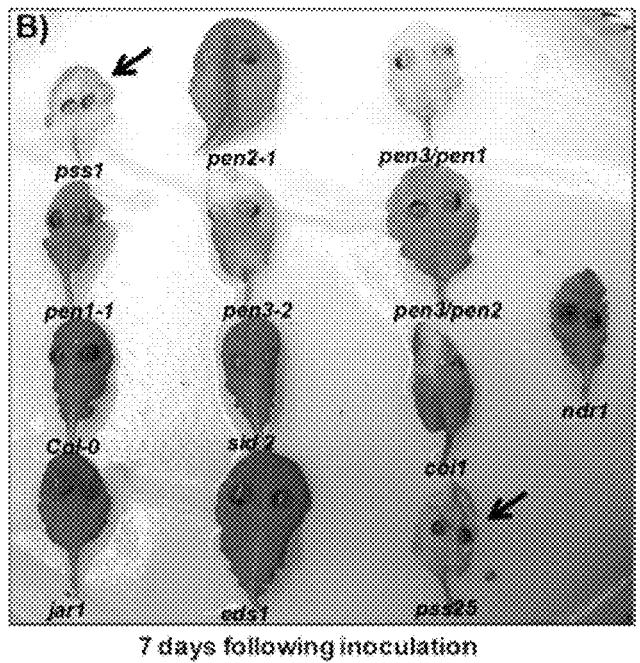
Figures 3A, 3B:
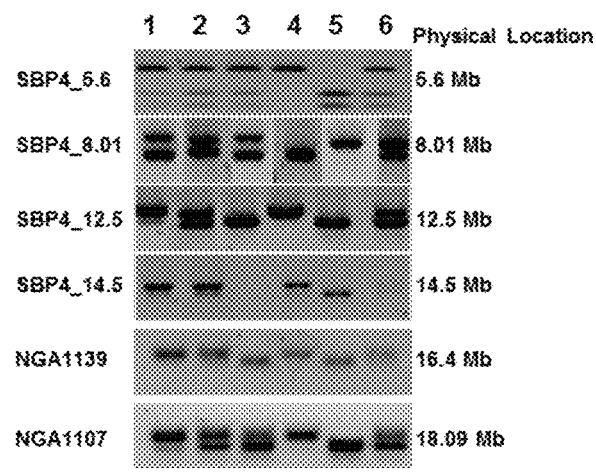
FIGS. 3A-3C show the molecular mapping of the Pss25 locus.
Figure 3C:
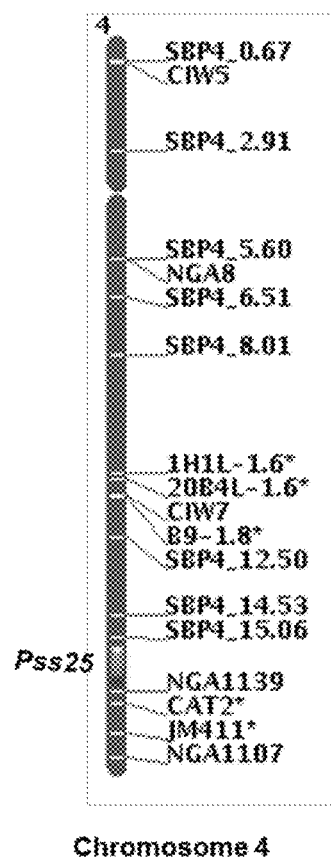

The present invention provides for isolated nucleic acid molecules comprising nucleotide sequences encoding the amino acid sequence herein: Pss6-At4g15780 (vesicle-associated membrane protein 724) (SEQ ID NOS: 1 and 2); Pss21-At5g64940 (oxidative stress-related abc1-like protein 1) (SEQ ID NOS: 3 and 4) and Pss25 At4g36870 (BLH2-BEL1-like homeodomain protein 2) (SEQ ID NOS 5 and 6) and any conservatively modified variants, fragments, and homologs or full length sequences incorporating the same which retain the Phyphthora infection related activity described herein. Further provided are polypeptides having an amino acid sequence encoded by a nucleic acid molecule described herein, for example those polypeptides comprising the sequences set forth in the herein, and fragments and variants thereof.

The invention encompasses isolated or substantially purified nucleic acid or protein compositions. An "isolated" or "purified" nucleic acid molecule or protein, or biologically active portion thereof, is substantially free of other cellular material, or culture medium when produced by recombinant techniques, or substantially free of chemical precursors or other chemicals when chemically synthesized. In some embodiments, an "isolated" nucleic acid is free of sequences (such as other protein-encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, 0.4 kb, 0.3 kb, 0.2 kb, or 0.1 kb, or 50, 40, 30, 20, or 10 nucleotides that naturally flank the nucleic acid molecule in genomic DNA of the cell from which the nucleic acid is derived. A protein that is substantially free of cellular material includes preparations of protein having less than about 30%, 20%, 10%, 5%, (by dry weight) of contaminating protein. When the protein of the invention or biologically active portion thereof is recombinantly produced, culture medium may represent less than about 30%, 20%, 10%, or 5% (by dry weight) of chemical precursors or non-protein-of-interest chemicals.

Fragments and variants of the disclosed nucleotide sequences are encompassed by the present invention. Fragments and variants of proteins encoded by the disclosed nucleotide sequences are also encompassed by the present invention. By "fragment" is intended a portion of the nucleotide sequence or a portion of the amino acid sequence and hence protein encoded thereby. Fragments of a nucleotide sequence may encode protein fragments that retain the biological activity of the native protein and hence affect development, developmental pathways, stress responses, and/or disease resistance by retaining Non host resistance-like activity. Alternatively, fragments of a nucleotide sequence that are useful as hybridization probes generally do not encode fragment proteins retaining biological activity. Thus, fragments of a nucleotide sequence may range from at least about 20 nucleotides, about 50 nucleotides, about 100 nucleotides, and up to the full-length nucleotide sequence encoding the proteins of the invention.

A fragment of a non host resistance nucleotide sequence that encodes a biologically active portion of a non host resistance protein of the invention will encode at least 12, 25, 30, 50, 75, etc. contiguous amino acids, or up to the total number of amino acids present in a full-length non host resistance protein of the invention.

Fragments of a non host resistance nucleotide sequence that are useful as hybridization probes or PCR primers generally may or may not encode a biologically active portion of a protein. Thus, a fragment of a non host resistance protein nucleotide sequence may encode a biologically active portion of a non host resistance protein, or it may be used as a hybridization probe or PCR primer using methods disclosed below. A biologically active portion of a non host resistance protein can be prepared by isolating a portion of the Non host resistance nucleotide sequences of the invention, expressing the encoded portion of the Non host resistance protein (e.g., by recombinant expression in vitro), and assessing the activity of the encoded portion of the Non host resistance protein. Nucleic acid molecules that are fragments of a Non host resistance nucleotide sequence comprise at least 16, 20, 25, 30, 40, 50, 60, 70, 80, 90, 100, 125, 150, 175, 200, etc. nucleotides, or up to the number of nucleotides present in a full-length Non host resistance nucleotide sequences disclosed herein.

The proteins of the invention may be altered in various ways including amino acid substitutions, deletions, truncations, and insertions. Methods for such manipulations are generally known in the art. For example, amino acid sequence variants of the Nonhost resistance proteins can be prepared by mutations in the DNA. Methods for mutagenesis and nucleotide sequence alterations are well known in the art. See, for example, Kunkel (1985) *Proc. Nat. Acad. Sci. USA* 82:488-492; Kunkel et al. (1987) *Methods in Enzymol.* 154:367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be made.

It is recognized that having identified the nucleotide sequences disclosed herein, it is within the state of the art to isolate and identify regulatory elements in the 5' untranslated region upstream from regions defined herein. Thus for example, the promoter regions of the gene sequences disclosed herein may further comprise upstream regulatory elements that confer tissue-preferred expression of heterologous nucleotide sequences operably linked to the disclosed promoter sequence. See particularly, Australian Patent No. AU-A-77751/94 and U.S. Pat. Nos. 5,466,785 and 5,635,618. It is also recognized by those of skill in the art that regulatory elements may be found in transcribed regions of a gene, for example in the region between transcription start and translation start as well as 3' to the end of translation; such elements may be found in the sequences set forth herein.

The nucleotide sequences of the invention can be used to isolate corresponding sequences from other organisms, particularly other plants, more particularly other crop plants. In this manner, methods such as PCR, hybridization, and the like can be used to identify such sequences based on their sequence homology to the sequences set forth herein. Sequences isolated based on their sequence identity to the nucleotide sequences set forth herein or to fragments thereof are encompassed by the present invention. Such sequences include sequences that are orthologs of the disclosed sequences. By "orthologs" is intended genes derived from a common ancestral gene and which are found in different species as a result of speciation. Genes found in different species are considered orthologs when their nucleotide sequences and/or their encoded protein sequences share substantial identity as defined elsewhere herein. Functions of orthologs are often highly conserved among species. Thus, isolated sequences that have Non host resistance-like activity or and which hybridize under stringent conditions to the Non host resistance sequences disclosed herein, or to fragments thereof, are encompassed by the present invention.

In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known nucleotide sequence is used as a probe that selectively hybridizes to other corresponding nucleotide sequences present it a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on the disease-resistant sequences of the invention. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.).

For example, an entire sequence disclosed herein, or one or more portions thereof, may be used as a probe capable of specifically hybridizing to corresponding *Fusarium*-response sequences, including promoters and messenger RNAs. To achieve specific hybridization under a variety of conditions, such probes include sequences that are unique among *Fusarium*-response sequences and may be at least about 10 or 15 or 17 nucleotides in length or at least about 20 or 22 or 25 nucleotides in length. Such probes may be used to amplify corresponding sequences from a chosen organism by PCR. This technique may be used to isolate additional coding sequences from a desired organism or as a diagnostic assay to determine the presence of coding sequences in an organism. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Plainview, N.Y.).

Assays that measure antipathogenic activity induced by the signal pathway from the sequences herein are commonly known in the art, as are methods to quantitate disease resistance in plants following pathogen infection. See, for example, U.S. Pat. No. 5,614,395, herein incorporated by reference. These assays may be used to measure the activity of the polypeptides of the invention. Such techniques include, measuring over time, the average lesion diameter, the pathogen biomass, and the overall percentage of decayed plant tissues. For example, a plant either expressing an antipathogenic polypeptide or having an antipathogenic composition applied to its surface shows a decrease in tissue necrosis (i.e., lesion diameter) or a decrease in plant death following pathogen challenge when compared to a control plant that was not exposed to the antipathogenic composition. Alternatively, antipathogenic activity can be measured by a decrease in pathogen biomass. For example, a plant expressing an antipathogenic polypeptide or exposed to an antipathogenic composition is challenged with a pathogen of interest. Over time, tissue samples from the pathogen-inoculated tissues are obtained and RNA is extracted. The percent of a specific pathogen RNA transcript relative to the level of a plant specific transcript allows the level of pathogen biomass to be determined. See, for example, Thomma et al. (1998) *Plant Biology* 95:15107-15111, herein incorporated by reference.

Furthermore, in vitro antipathogenic assays include, for example, the addition of varying concentrations of the antipathogenic proteins to paper disks and placing the disks on agar containing a suspension of the pathogen of interest. Following incubation, clear inhibition zones develop around the discs that contain an effective concentration of the antipathogenic polypeptide (Liu et al. (1994) *Plant Biology* 91:1888-1892, herein incorporated by reference). Additionally, microspectrophotometrical analysis can be used to measure the in vitro antipathogenic properties of a composition (Hu et al. (1997) *Plant Mol. Biol.* 34:949-959 and Cammue et al. (1992) *J. Biol. Chem.* 267: 2228-2233, both of which are herein incorporated by reference).

Pathogens of the invention include, but are not limited to, fungal and viral pathogens for primarily soybeans which include: *Fusarium sojae, Macrophomina phaseolina, Rhizoctonia solani, Sclerotinia sclerotiorum, Fusarium virguliformae, (Fusarium solani) Diaporthe phaseolorum* var. *sojae (Phomopsis sojae), Diaporthe phaseolorum* var. *caulivora, Sclerotium rolfsii, Cercospora kikuchii, Cercospora sojina, Peronospora manshurica, Colletotrichum dematium (Colletotichum truncatum), Corynespora cassfcola, Septoria glycines, Phyllosticta sojicola, Alternaria alternata, Pseudomonas syringae* p. v. *glycinea, Xanthomonas campestris* p. v. *phaseoli, Microsphaera diffusa, Fusarium semitectum, Phialophora gregata,* Soybean mosaic virus, *Glomerella glycines,* Tobacco Ring spot virus, Tobacco Streak virus, *Phakopsora pachyrhizi, Phakopsora meibomiae, Pythium aphanidermatum, Pythium ultimum, Pythium debaryanum,* Tomato spotted wilt virus, *Heterodera glycines.*

It is understood in the art that plant DNA viruses and fungal pathogens remodel the control of the host replication and gene expression machinery to accomplish their own replication and effective infection. The plant response to stress, such as stress caused by *Fusarium* attack, is known to involve many basic biochemical pathways and cellular functions. Hence, the sequences of the invention may find use in altering the defense mechanisms of a host plant to provide broad-based resistance to disease or insect pests. Additionally, the present invention may be useful in preventing corruption of the cell machinery by viruses and other plant pathogens.

The compositions and methods of the invention function to inhibit or prevent plant diseases. The gene products may accomplish their anti-pathogenic effects by suppressing, controlling, and/or killing the invading pathogenic organism in non host plants and these sequence may then be used to engineer resistance in susceptible plants.

The cells that have been transformed may be grown into plants in accordance with conventional ways. See, for example, McCormick et al. (1986) Plant Cell Reports 5:8184. These plants may then be grown, and either pollinated with the same transformed strain or different strains, and the resulting hybrid having constitutive expression of the desired phenotypic characteristic identified. Two or more generations may be grown to ensure that constitutive expression of the desired phenotypic characteristic is stably maintained and inherited and then seeds harvested to ensure constitutive expression of the desired phenotypic characteristic has been achieved.

The invention in one aspect comprises expression constructs comprising a DNA sequence which encodes upon expression a Nonhost resistance nucleic acid sequence operably linked to a promoter to direct expression of the protein. These constructs are then introduced into plant cells using standard molecular biology techniques. The invention can be also be used for hybrid plant or seed production, once transgenic inbred parental lines have been established.

The methods of the invention described herein may be applicable to any species of plant.

Production of a genetically modified plant tissue either expressing or inhibiting expression of a structural gene combines the teachings of the present disclosure with a variety of techniques and expedients known in the art. In most instances, alternate expedients exist for each stage of the overall process. The choice of expedients depends on the variables such as the plasmid vector system chosen for the cloning and introduction of the recombinant DNA molecule, the plant species to be modified, the particular structural gene, promoter elements and upstream elements used. Persons skilled in the art are able to select and use appropriate alternatives to achieve functionality. Culture conditions for expressing desired structural genes and cultured cells are known in the art. Also as known in the art, a number of both monocotyledonous and dicotyledonous plant species are transformable and regenerable such that whole plants containing and expressing desired genes under regulatory control of the promoter molecules according to the invention may be obtained. As is known to those of skill in the art, expression in transformed plants may be tissue specific and/or specific to certain developmental stages. Truncated promoter selection and structural gene selection are other parameters which may be optimized to achieve desired plant expression or inhibition as is known to those of skill in the art and taught herein.

The following is a non-limiting general overview of Molecular biology techniques which may be used in performing the methods of the invention.

Promoters

The constructs, promoters or control systems used in the methods of the invention may include a tissue specific promoter, an inducible promoter or a constitutive promoter.

A large number of suitable promoter systems are available. For example one constitutive promoter useful for the invention is the cauliflower mosaic virus (CaMV) 35S. It has been shown to be highly active in many plant organs and during many stages of development when integrated into the genome of transgenic plants and has been shown to confer expression in protoplasts of both dicots and monocots.

Organ-specific promoters are also well known. For example, the E8 promoter is only transcriptionally activated during tomato fruit ripening, and can be used to target gene expression in ripening tomato fruit (Deikman and Fischer, *EMBO J.* (1988) 7:3315; Giovannoni et al., *The Plant Cell* (1989) 1:53). The activity of the E8 promoter is not limited to tomato fruit, but is thought to be compatible with any system wherein ethylene activates biological processes. Similarly the Lipoxegenase ("the LOX gene") is a fruit specific promoter.

Other fruit specific promoters are the 1.45 promoter fragment disclosed in Bird, et al., *Plant Mol. Bio.*, pp 651-663(1988) and the polygalacturonase promoter from tomato disclosed in U.S. Pat. No. 5,413,937 to Bridges et al.

Leaf specific promoters include as the AS-1 promoter disclosed in U.S. Pat. No. 5,256,558 to Coruzzi and the RBCS-3A promoter isolated from pea the RBCS-3A gene disclosed in U.S. Pat. No. 5,023,179 to Lam et al.

And finally root specific promoters include the CamV 35S promoter disclosed in U.S. Pat. No. 391,725 to Coruzzi et al; the RB7 promoter disclosed in U.S. Pat. No. 5,459,252 to Conking et al and the promoter isolated from *Brassica napus* disclosed in U.S. Pat. No. 5,401,836 to Bazczynski et al. which give root specific expression.

Other examples of promoters include maternal tissue promoters such as seed coat, pericarp and ovule. Promoters highly expressed early in endosperm development are most effective in this application. Of particular interest is the promoter from the a' subunit of the soybean β-conglycinin gene [Walling et al., *Proc. Natl. Acad. Sci. USA* 83:2123-2127 (1986)] which is expressed early in seed development in the endosperm and the embryo.

Further seed specific promoters include the Napin promoter described in U.S. Pat. No. 5,110,728 to Calgene, which describes and discloses the use of the napin promoter in directing the expression to seed tissue of an acyl carrier protein to enhance seed oil production; the DC3 promoter from carrots which is early to mid embryo specific and is disclosed at *Plant Physiology*, October 1992 100(2) p. 576-581, "Hormonal and Environmental Regulation of the Carrot Lea-class Gene Dc 3, and *Plant Mol. Biol.*, April 1992, 18(6) p. 1049-1063, "Transcriptional Regulation of a Seed Specific Carrot Gene, DC 8": the phaseolin promoter described in U.S. Pat. No. 5,504,200 to Mycogen which discloses the gene sequence and regulatory regions for phaseolin, a protein isolated from *P. vulgaris* which is expressed only while the seed is developing within the pod, and only in tissues involved in seed generation.

Other organ-specific promoters appropriate for a desired target organ can be isolated using known procedures. These control sequences are generally associated with genes uniquely expressed in the desired organ. In a typical higher plant, each organ has thousands of mRNAs that are absent from other organ systems (reviewed in Goldberg, Phil, *Trans. R. Soc. London* (1986) B314-343. mRNAs are first isolated to obtain suitable probes for retrieval of the appropriate genomic sequence which retains the presence of the natively associated control sequences. An example of the use of techniques to obtain the cDNA associated with mRNA specific to avocado fruit is found in Christoffersen et al., *Plant Molecular Biology* (1984) 3:385. Briefly, mRNA was isolated from ripening avocado fruit and used to make a cDNA library. Clones in the library were identified that hybridized with labeled RNA isolated from ripening avocado fruit, but that did not hybridize with labeled RNAs isolated from unripe avocado fruit. Many of these clones represent mRNAs encoded by genes that are transcriptionally activated at the onset of avocado fruit ripening.

Another very important method that can be used to identify cell type specific promoters that allow even to identification of genes expressed in a single cell is enhancer detection (O'Kane, C., and Gehring, W. J. (1987), "Detection in situ of genomic regulatory elements in *Drosophila*", *Proc. Natl. Acad. Sci. USA*, 84, 9123-9127). This method was first developed in *Drosophila* and rapidly adapted to mice and plants (Wilson, C., Pearson, R. K., Bellen, H. J., O'Kane, C. J., Grossniklaus, U., and Gehring, W. J. (1989), "P-element-mediated enhancer detection: an efficient method for isolating and characterizing developmentally regulated genes in *Drosophila*", *Genes & Dev.*, 3, 1301-1313; Skarnes, W. C. (1990), "Entrapment vectors: a new tool for mammalian genetics", *Biotechnology*, 8, 827-831; Topping, J. F., Wei, W., and Lindsey, K. (1991), "Functional tagging of regulatory elements in the plant genome", *Development*, 112, 1009-1019; Sundaresan, V., Springer, P. S., Volpe, T., Haward, S., Jones, J. D. G., Dean, C., Ma, H., and Martienssen, R. A., (1995), "Patterns of gene action in plant development revealed by enhancer trap and gene trap transposable elements", *Genes & Dev.*, 9, 1797-1810).

The promoter used in the method of the invention may be an inducible promoter. An inducible promoter is a promoter that is capable of directly or indirectly activating transcription of a DNA sequence in response to an inducer. In the absence of an inducer, the DNA sequence will not be transcribed. Typically, the protein factor that binds specifically to an inducible promoter to activate transcription is present in an inactive form which is then directly or indirectly converted to the active form by the inducer. The inducer may be a chemical agent such as a protein, metabolite (sugar, alcohol etc.), a growth regulator, herbicide, or a phenolic compound or a physiological stress imposed directly by heat, salt, toxic elements etc. or indirectly through the action of a pathogen or disease agent such as a virus. A plant cell containing an inducible promoter may be exposed to an inducer by externally applying the inducer to the cell such as by spraying, watering, heating, or similar methods. Examples of inducible promoters include the inducible 70 kd heat shock promoter of *D. melanogaster* (Freeling, M., Bennet, D. C., Maize ADN 1, *Ann. Rev. of Genetics*, 19:297-323) and the alcohol dehydrogenase promoter which is induced by ethanol (Nagao, R. T., et al., Miflin, B. J., Ed. Oxford Surveys of Plant Molecular and Cell Biology, Vol. 3, p. 384-438, Oxford University Press, Oxford 1986) or the Lex A promoter which is triggered with chemical treatment and is available through Ligand pharmaceuticals. The inducible promoter may be in an induced state throughout seed formation or at least for a period which corresponds to the transcription of the DNA sequence of the recombinant DNA molecule(s).

Another example of an inducible promoter is the chemically inducible gene promoter sequence isolated from a 27 kd subunit of the maize glutathione-S-transferase (GST II) gene. Two of the inducers for this promoter are N,N-diallyl-2,2-dichloroacetamide (common name: dichloramid) or benzyl-=2-chloro-4-(trifluoromethyl)-5-thiazolecarboxylate (common name: flurazole). In addition, a number of other potential inducers may be used with this promoter as described in published PCT Application No. PCT/GB90/00110 by ICI.

Another example of an inducible promoter is the light inducible chlorophyll a/b binding protein (CAB) promoter, also described in published PCT Application No. PCT/GB90/00110 by ICI.

Inducible promoters have also been described in published Application No. EP89/103888.7 by Ciba-Geigy. In this application, a number of inducible promoters are identified, including the PR protein genes, especially the tobacco PR protein genes, such as PR-1a, PR-1b, PR-1c, PR-1, PR-A, PR-S, the cucumber chitinase gene, and the acidic and basic tobacco beta-1,3-glucanase genes. There are numerous potential inducers for these promoters, as described in Application No. EP89/103888.7.

The preferred promoters may be used in conjunction with naturally occurring flanking coding or transcribed sequences of the feronia regulatory genes or with any other coding or transcribed sequence that is critical to pollin tube formation and/or fertilization.

It may also be desirable to include some intron sequences in the promoter constructs since the inclusion of intron sequences in the coding region may result in enhanced expression and specificity. Thus, it may be advantageous to join the DNA sequences to be expressed to a promoter sequence that contains the first intron and exon sequences of a polypeptide which is unique to cells/tissues of a plant critical to female gametophyte development and/or function.

Additionally, regions of one promoter may be joined to regions from a different promoter in order to obtain the desired promoter activity resulting in a chimeric promoter. Synthetic promoters which regulate gene expression may also be used.

The expression system may be further optimized by employing supplemental elements such as transcription terminators and/or enhancer elements.

Other Regulatory Elements

In addition to a promoter sequence, an expression cassette or construct should also contain a transcription termination region downstream of the structural gene to provide for efficient termination. The termination region or polyadenylation signal may be obtained from the same gene as the promoter sequence or may be obtained from different genes. Polyadenylation sequences include, but are not limited to the *Agrobacterium* octopine synthase signal (Gielen et al., *EMBO J.* (1984) 3:835-846) or the nopaline synthase signal (Depicker et al., *Mol. and Appl. Genet.* (1982) 1:561-573).

Marker Genes

Recombinant DNA molecules containing any of the DNA sequences and promoters described herein may additionally contain selection marker genes which encode a selection gene product which confer on a plant cell resistance to a chemical agent or physiological stress, or confers a distinguishable phenotypic characteristic to the cells such that plant cells transformed with the recombinant DNA molecule may be easily selected using a selective agent. One such selection marker gene is neomycin phosphotransferase (NPT II) which confers resistance to kanamycin and the antibiotic G-418. Cells transformed with this selection marker gene may be selected for by assaying for the presence in vitro of phosphorylation of kanamycin using techniques described in the literature or by testing for the presence of the mRNA coding for the NPT II gene by Northern blot analysis in RNA from the tissue of the transformed plant. Polymerase chain reactions are also used to identify the presence of a transgene or expression using reverse transcriptase PCR amplification to monitor expression and PCR on genomic DNA. Other commonly used selection markers include the ampicillin resistance gene, the tetracycline resistance and the hygromycin resistance gene. Transformed plant cells thus selected can be induced to differentiate into plant structures which will eventually yield whole plants. It is to be understood that a selection marker gene may also be native to a plant.

Transformation

Numerous methods for plant transformation have been developed, including biological and physical, plant transformation protocols. See, for example, Miki et al., "Procedures for Introducing Foreign DNA into Plants" in *Methods in Plant Molecular Biology and Biotechnology*, Glick, B. R. and Thompson, J. E. Eds. (CRC Press, Inc., Boca Raton, 1993) pages 67-88. In addition, expression vectors and in vitro culture methods for plant cell or tissue transformation and regeneration of plants are available. See, for example, Gruber et al., "Vectors for Plant Transformation" in *Methods in Plant Molecular Biology and Biotechnology*, Glick, B. R. and Thompson, J. E. Eds. (CRC Press, Inc., Boca Raton, 1993) pages 89-119.

A. *Agrobacterium*-Mediated Transformation

One method for introducing an expression vector into plants is based on the natural transformation system of *Agrobacterium*. See, for example, Horsch et al., *Science* 227: 1229 (1985). *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., *Crit. Rev. Plant. Sci.* 10: 1 (1991). Descriptions of *Agrobacterium* vector systems and methods for *Agrobacterium*-mediated gene transfer are provided by Gruber et al., supra, Miki et al., supra, and Moloney et al., *Plant Cell Reports* 8: 238 (1989). See also, U.S. Pat. No. 5,563,055, (Townsend and Thomas), issued Oct. 8, 1996.

B. Direct Gene Transfer

Several methods of plant transformation, collectively referred to as direct gene transfer, have been developed as an alternative to *Agrobacterium*-mediated transformation.

A generally applicable method of plant transformation is microprojectile-mediated transformation wherein DNA is carried on the surface of microprojectiles measuring 1 to 4 □m. The expression vector is introduced into plant tissues with a biolistic device that accelerates the microprojectiles to speeds of 300 to 600 m/s which is sufficient to penetrate plant cell walls and membranes. Sanford et al., *Part. Sci. Technol.* 5: 27 (1987), Sanford, J. C., *Trends Biotech.* 6: 299 (1988), Klein et al., *Bio/Technology* 6: 559-563 (1988), Sanford, J. C., *Physiol Plant* 79: 206 (1990), Klein et al., *Biotechnology* 10: 268 (1992). See also U.S. Pat. No. 5,015,580 (Christou, et al), issued May 14, 1991; U.S. Pat. No. 5,322,783 (Tomes, et al.), issued Jun. 21, 1994.

Another method for physical delivery of DNA to plants is sonication of target cells. Zhang et al., *Bio/Technology* 9: 996 (1991). Alternatively, liposome or spheroplast fusion have been used to introduce expression vectors into plants. Deshayes et al., *EMBO J.*, 4: 2731 (1985), Christou et al., *Proc Natl. Acad. Sci. U.S.A.* 84: 3962 (1987). Direct uptake of DNA into protoplasts using CaCl2 precipitation, polyvinyl alcohol or poly-L-ornithine have also been reported. Hain et al., *Mol. Gen. Genet.* 199: 161 (1985) and Draper et al., *Plant Cell Physiol.* 23: 451 (1982). Electroporation of protoplasts and whole cells and tissues have also been described. Donn et al., In Abstracts of VIIth International Congress on Plant Cell and Tissue Culture IAPTC, A2-38, p 53 (1990); D'Halluin et al., *Plant Cell* 4: 1495-1505 (1992) and Spencer et al., *Plant Mol. Biol.* 24: 51-61 (1994).

Following transformation of target tissues, expression of the above-described selectable marker genes allows for preferential selection of transformed cells, tissues and/or plants, using regeneration and selection methods now well known in the art.

It is often desirable to have the DNA sequence in homozygous state which may require more than one transformation event to create a parental line, requiring transformation with a first and second recombinant DNA molecule both of which encode the same gene product. It is further contemplated in some of the embodiments of the process of the invention that a plant cell be transformed with a recombinant DNA molecule containing at least two DNA sequences or be transformed with more than one recombinant DNA molecule. The DNA sequences or recombinant DNA molecules in such embodiments may be physically linked, by being in the same vector, or physically separate on different vectors. A cell may be simultaneously transformed with more than one vector provided that each vector has a unique selection marker gene. Alternatively, a cell may be transformed with more than one vector sequentially allowing an intermediate regeneration step after transformation with the first vector. Further, it may be possible to perform a sexual cross between individual plants or plant lines containing different DNA sequences or recombinant DNA molecules preferably the DNA sequences or the recombinant DNA molecules are linked or located on the same chromosome, and then selecting from the progeny of the cross, plants containing both DNA sequences or recombinant DNA molecules.

Expression of recombinant DNA molecules containing the DNA sequences and promoters described herein in transformed plant cells may be monitored using Northern blot techniques and/or Southern blot techniques known to those of skill in the art.

The transformed cells may then be regenerated into a transgenic plant. The regenerated plants are transferred to standard soil conditions and cultivated in a conventional manner.

After the expression or inhibition cassette is stably incorporated into regenerated transgenic plants, it can be transferred to other plants by sexual crossing. Any of a number of standard breeding techniques can be used, depending upon the species to be crossed.

It may be useful to generate a number of individual transformed plants with any recombinant construct in order to recover plants free from any position effects. It may also be preferable to select plants that contain more than one copy of the introduced recombinant DNA molecule such that high levels of expression of the recombinant molecule are obtained.

As indicated above, it may be desirable to produce plant lines which are homozygous for a particular gene. In some species this is accomplished rather easily by the use of another culture or isolated microspore culture. This is especially true for the oil seed crop *Brassica napus* (Keller and Armstrong, Z. *flanzenzucht* 80:100-108, 1978). By using these techniques, it is possible to produce a haploid line that carries the inserted gene and then to double the chromosome number either spontaneously or by the use of colchicine. This gives rise to a plant that is homozygous for the inserted gene, which can be easily assayed for if the inserted gene carries with it a suitable selection marker gene for detection of plants carrying that gene. Alternatively, plants may be self-fertilized, leading to the production of a mixture of seed that consists of, in the simplest case, three types, homozygous (25%), heterozygous (50%) and null (25%) for the inserted gene. Although it is relatively easy to score null plants from those that contain the gene, it is possible in practice to score the homozygous from heterozygous plants by southern blot analysis in which careful attention is paid to the loading of exactly equivalent amounts of DNA from the mixed population, and scoring heterozygotes by the intensity of the signal from a probe specific for the inserted gene. It is advisable to verify the results of the southern blot analysis by allowing each independent transformant to self-fertilize, since additional evidence for homozygosity can be obtained by the simple fact that if the plant was homozygous for the inserted gene, all of the subsequent plants from the selfed seed will contain the gene, while if the plant was heterozygous for the gene, the generation grown from the selfed seed will contain null plants. Therefore, with simple selfing one can easily select homozygous plant lines that can also be confirmed by southern blot analysis.

Creation of homozygous parental lines makes possible the production of hybrid plants and seeds which will contain a modified protein component. Transgenic homozygous parental lines are maintained with each parent containing either the first or second recombinant DNA sequence operably linked to a promoter. Also incorporated in this scheme are the advantages of growing a hybrid crop, including the combining of more valuable traits and hybrid vigor.

The nucleotide constructs of the invention also encompass nucleotide constructs that may be employed in methods for altering or mutating a genomic nucleotide sequence in an organism, including, but not limited to, chimeric vectors, chimeric mutational vectors, chimeric repair vectors, mixed-duplex oligonucleotides, self-complementary chimeric oligonucleotides, and recombinogenic oligonucleobases. Such nucleotide constructs and methods of use, such as, for example, chimeraplasty, are known in the art. Chimeraplasty involves the use of such nucleotide constructs to introduce site-specific changes into the sequence of genomic DNA within an organism. See, U.S. Pat. Nos. 5,565,350; 5,731,181; 5,756,325; 5,760,012; 5,795,972; and 5,871,984; all of which are herein incorporated by reference. See also, WO 98/49350, WO 99/07865, WO 99/25821, and Beetham et al. (1999) *Proc. Natl. Acad. Sci. USA* 96:8774-8778; herein incorporated by reference.

Molecular Markers

The present invention provides a method of genotyping a plant comprising a heterologous polynucleotide of the present invention. Genotyping provides a means of distinguishing homologs of a chromosome pair and can be used to differentiate segregants in a plant population. Molecular marker methods can be used for phylogenetic studies, characterizing genetic relationships among crop varieties, identifying crosses or somatic hybrids, localizing chromosomal segments affecting monogenic traits, map based cloning, and the study of quantitative inheritance. See, e. g., Clark, Ed., Plant Molecular Biology: A Laboratory Manual. Berlin, Springer Verlag, 1997. Chapter 7. For molecular marker methods, see generally, "The DNA Revolution" in: Paterson, A. H., Genome Mapping in Plants (Austin, Tex., Academic Press/R. G. Landis Company, 1996) pp. 7-21.

The particular method of genotyping in the present invention may employ any number of molecular marker analytic techniques such as, but not limited to, restriction fragment length polymorphisms (RFLPs). RFLPs are the product of allelic differences between DNA restriction fragments resulting from nucleotide sequence variability. As is well known to those of skill in the art, RFLPs are typically detected by extraction of genomic DNA and digestion with a restriction enzyme. Generally, the resulting fragments are separated according to size and hybridized with a probe; single copy probes are preferred. Restriction fragments from homologous chromosomes are revealed.

Differences in fragment size among alleles represent an RFLP. Thus, the present invention further provides a means to follow segregation of a gene or nucleic acid of the present invention as well as chromosomal sequences genetically linked to these genes or nucleic acids using such techniques as RFLP analysis. Linked chromosomal sequences are within 50 centiMorgans (cM), often within 40 or 30 cM, preferably within 20 or 10 cM, more preferably within 5, 3, 2, or 1 cM of a gene of the present invention.

In the present invention, the nucleic acid probes employed for molecular marker mapping of plant nuclear genomes selectively hybridize, under selective hybridization conditions, to a gene encoding a polynucleotide of the present invention. In preferred embodiments, the probes are selected from polynucleotides of the present invention.

Typically, these probes are cDNA probes or restriction-enzyme treated (e. g., PstI) genomic clones. The length of the probes is discussed in greater detail, supra, but are typically at least 15 bases in length, more preferably at least 20, 25, 30, 35, 40, or 50 bases in length. Generally, however, the probes are less than about 1 kilobase in length. Preferably, the probes are single copy probes that hybridize to a unique locus in a haploid chromosome complement. Some exemplary restriction enzymes employed in RFLP mapping are EcoRI, EcoRv, and SstI. As used herein the term "restriction enzyme" includes reference to a composition that recognizes and, alone or in conjunction with another composition, cleaves at a specific nucleotide sequence.

The method of detecting an RFLP comprises the steps of (a) digesting genomic DNA of a plant with a restriction enzyme; (b) hybridizing a nucleic acid probe, under selective hybridization conditions, to a sequence of a polynucleotide of the present of said genomic DNA; (c) detecting therefrom a RFLP. Other methods of differentiating polymorphic (allelic) variants of polynucleotides of the present invention can be had by utilizing molecular marker techniques well known to those of skill in the art including such techniques as: 1) single stranded conformation analysis (SSCA); 2) denaturing gradient gel electrophoresis (DGGE); 3) RNase protection assays; 4) allele-specific oligonucleotides (ASOs); 5) the use of proteins which recognize nucleotide mismatches, such as the *E. coli* mutS protein; and 6) allele-specific PCR. Other approaches based on the detection of mismatches between the two complementary DNA strands include clamped denaturing gel electrophoresis (CDGE); heteroduplex analysis (HA); and chemical mismatch cleavage (CMC). Thus, the present invention further provides a method of genotyping comprising the steps of contacting, under stringent hybridization conditions, a sample suspected of comprising a polynucleotide of the present invention with a nucleic acid probe. Generally, the sample is a plant sample; preferably, a sample suspected of comprising a maize polynucleotide of the present invention (e. g., gene, mRNA). The nucleic acid probe selectively hybridizes, under stringent conditions, to a subsequence of a polynucleotide of the present invention comprising a polymorphic marker. Selective hybridization of the nucleic acid probe to the polymorphic marker nucleic acid sequence yields a hybridization complex. Detection of the hybridization complex indicates the presence of that polymorphic marker in the sample. In preferred embodiments, the nucleic acid probe comprises a polynucleotide of the present invention.

UTRs and Codon Preference

In general, translational efficiency has been found to be regulated by specific sequence elements in the 5' non-coding or untranslated region (5'UTR) of the RNA. Positive sequence motifs include translational initiation consensus sequences (Kozak, Nucleic Acids Res. 15: 8125 (1987)) and the 7-methylguanosine cap structure (Drummond et al., Nucleic Acids Res. 13: 7375 (1985)). Negative elements include stable intramolecular 5'UTR stem-loop structures (Muesing et al., Cell 48: 691 (1987)) and AUG sequences or short open reading frames preceded by an appropriate AUG in the 5'UTR (Kozak, supra, Rao et al., Mol. and Cell. Biol. 8: 284 (1988)). Accordingly, the present invention provides 5' and/or 3' untranslated regions for modulation of translation of heterologous coding sequences.

Further, the polypeptide-encoding segments of the polynucleotides of the present invention can be modified to alter codon usage. Altered codon usage can be employed to alter translational efficiency and/or to optimize the coding sequence for expression in a desired host such as to optimize the codon usage in a heterologous sequence for expression in maize. Codon usage in the coding regions of the polynucleotides of the present invention can be analyzed statistically using commercially available software packages such as "Codon Preference" available from the University of Wisconsin Genetics Computer Group (see Devereaux et al., Nucleic Acids Res. 12: 387-395 (1984)) or MacVector 4.1 (Eastman Kodak Co., New Haven, Conn.). Thus, the present invention provides a codon usage frequency characteristic of the coding region of at least one of the polynucleotides of the present invention. The number of polynucleotides that can be used to determine a codon usage frequency can be any integer from 1 to the number of polynucleotides of the present invention as provided herein. Optionally, the polynucleotides will be full-length sequences. An exemplary number of sequences for statistical analysis can be at least 1, 5, 10, 20, 50, or 100.

Sequence Shuffling

The present invention provides methods for sequence shuffling using polynucleotides of the present invention, and compositions resulting therefrom. Sequence shuffling is described in PCT publication No. WO 97/20078. See also, Zhang, J.-H., et al. Proc. Natl. Acad. Sci. USA 94: 4504-4509 (1997). Generally, sequence shuffling provides a means for generating libraries of polynucleotides having a desired characteristic which can be selected or screened for. Libraries of recombinant polynucleotides are generated from a population of related sequence polynucleotides which comprise sequence regions which have substantial sequence identity and can be homologously recombined in vitro or in vivo. The population of sequence-recombined polynucleotides comprises a subpopulation of polynucleotides which possess desired or advantageous characteristics and which can be selected by a suitable selection or screening method. The characteristics can be any property or attribute capable of being selected for or detected in a screening system, and may include properties of: an encoded protein, a transcriptional element, a sequence controlling transcription, RNA processing, RNA stability, chromatin conformation, translation, or other expression property of a gene or transgene, a replicative element, a protein-binding element, or the like, such as any feature which confers a selectable or detectable property. In some embodiments, the selected characteristic will be a decreased Km and/or increased KCat over the wild-type protein as provided herein. In other embodiments, a protein or polynucleotide generated from sequence shuffling will have a ligand binding affinity greater than the non-shuffled wild-type polynucleotide. The increase in such properties can be at least 110%, 120%, 130%, 140% or at least 150% of the wild-type value.

Generic and Consensus Sequences

Polynucleotides and polypeptides of the present invention further include those having: (a) a generic sequence of at least two homologous polynucleotides or polypeptides, respectively, of the present invention; and, (b) a consensus sequence of at least three homologous polynucleotides or polypeptides, respectively, of the present invention. The generic sequence of the present invention comprises each species of polypeptide or polynucleotide embraced by the generic polypeptide or polynucleotide sequence, respectively. The individual species encompassed by a polynucleotide having an amino acid or nucleic acid consensus sequence can be used to generate antibodies or produce nucleic acid probes or primers to screen for homologs in other species, genera, families, orders, classes, phyla, or kingdoms.

Alternatively, a polynucleotide having a consensus sequence generated from orthologous genes can be used to identify or isolate orthologs of other taxa. Typically, a polynucleotide having a consensus sequence will be at least 25, 30, or 40 amino acids in length, or 20, 30, 40, 50, 100, or 150 nucleotides in length. As those of skill in the art are aware, a conservative amino acid substitution can be used for amino acids which differ amongst aligned sequence but are from the same conservative substitution group as discussed above. Optionally, no more than 1 or 2 conservative amino acids are substituted for each 10 amino acid length of consensus sequence.

Similar sequences used for generation of a consensus or generic sequence include any number and combination of allelic variants of the same gene, orthologous, or paralogous sequences as provided herein. Optionally, similar sequences used in generating a consensus or generic sequence are identified using the BLAST algorithm's smallest sum probability (P (N)). Various suppliers of sequence-analysis software are listed in chapter 7 of Current Protocols in Molecular Biology, F. M. Ausubel et al., Eds., Current Protocols, a joint venture between Greene Publishing Associates, Inc. and John Wiley & Sons, Inc. (Supplement 30).

A polynucleotide sequence is considered similar to a reference sequence if the smallest sum probability in a comparison of the test nucleic acid to the reference nucleic acid is less than about 0.1, more preferably less than about 0.01, or 0.001, and most preferably less than about 0.0001, or 0.00001. Similar polynucleotides can be aligned and a consensus or generic sequence generated using multiple sequence alignment software available from a number of commercial suppliers such as the Genetics Computer Group's (Madison, Wis.) PILEUP software, Vector NTI's (North Bethesda, Md.) ALIGNX, or Genecode's (Ann Arbor, Mich.) SEQUENCHER. Conveniently, default parameters of such software can be used to generate consensus or generic sequences.

Stacking

In certain embodiments the nucleic acid sequences of the embodiments can be stacked with any combination of polynucleotide sequences of interest in order to create plants with a desired phenotype. This stacking may be accomplished by a combination of genes within the DNA construct, or by crossing a line containing the nonhost resistance genes of the invention (as transgenes or as an introgressed locus), with another line that comprises the combination. For example, the polynucleotides of the embodiments may be stacked with any other polynucleotides of the embodiments, or with other genes. The combinations generated can also include multiple copies of any one of the polynucleotides of interest. The polynucleotides of the embodiments can also be stacked with any other gene or combination of genes to produce plants with a variety of desired trait combinations including and not limited to traits desirable for animal feed such as high oil genes (e.g., U.S. Pat. No. 6,232,529); balanced amino acids (e.g. hordothionins (U.S. Pat. Nos. 5,990,389; 5,885,801; 5,885,802; and 5,703,409); barley high lysine (Williamson et al. (1987) Eur. J. Biochem. 165:99-106; and WO 98/20122); and high methionine proteins (Pedersen et al. (1986) J. Biol. Chem. 261:6279; Kirihara et al. (1988) Gene 71:359; and Musumura et al. (1989) Plant Mol. Biol. 12: 123)); increased digestibility (e.g., modified storage proteins (U.S. application Ser. No. 10/053,410, filed Nov. 7, 2001); and thioredoxins (U.S. application Ser. No. 10/005,429, filed Dec. 3, 2001)), the disclosures of which are herein incorporated by reference. The polynucleotides of the embodiments can also be stacked with traits desirable for further insect, disease or herbicide resistance (e.g., *Bacillus thuringiensis* toxic proteins (U.S. Pat. Nos. 5,366,892; 5,747,450; 5,737,514; 5,723,756; 5,593,881; Geiser et al (1986) Gene 48:109); lectins (Van Damme et al. (1994) Plant Mol. Biol. 24:825); fumonisin detoxification genes (U.S. Pat. No. 5,792,931); avirulence and disease resistance genes (Jones et al. (1994) Science 266:789; Martin et al. (1993) Science 262:1432; Mindrinos et al. (1994) Cell 78:1089); acetolactate synthase (ALS) mutants that lead to herbicide resistance such as the S4 and/or Hra mutations; inhibitors of glutamine synthase such as phosphinothricin or basta (e.g., bar gene); and glyphosate resistance (EPSPS genes, GAT genes such as those disclosed in U.S. Patent Application Publication US2004/0082770, also WO02/36782 and WO03/092360)); and traits desirable for processing or process products such as high oil (e.g., U.S. Pat. No. 6,232,529); modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE) and starch debranching enzymes (SDBE)); and polymers or bioplastics (e.g., U.S. Pat. No. 5,602,321; beta-ketothiolase, polyhydroxybutyrate synthase, and acetoacetyl-CoA reductase (Schubert et al. (1988) J. Bacteriol. 170:5837-5847) facilitate expression of polyhydroxyalkanoates (PHAs)), the disclosures of which are herein incorporated by reference. One could also combine the polynucleotides of the embodiments with polynucleotides providing agronomic traits such as male sterility (e.g., see U.S. Pat. No. 5,583,210), stalk strength, flowering time, or transformation technology traits such as cell cycle regulation or gene targeting (e.g. WO 99/61619; WO 00/17364; WO 99/25821), the disclosures of which are herein incorporated by reference.

These stacked combinations can be created by any method including and not limited to cross breeding plants by any conventional or TOPCROSS® methodology, or genetic transformation. If the traits are stacked by genetically transforming the plants, the polynucleotide sequences of interest can be combined at any time and in any order. For example, a transgenic plant comprising one or more desired traits can be used as the target to introduce further traits by subsequent transformation. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant.

Use in Breeding Methods

The transformed plants of the invention may be used in a plant breeding program. The goal of plant breeding is to combine, in a single variety or hybrid, various desirable traits. For field crops, these traits may include, for example, resistance to diseases and insects, tolerance to heat and drought, reduced time to crop maturity, greater yield, and better agronomic quality. With mechanical harvesting of many crops, uniformity of plant characteristics such as germination and stand establishment, growth rate, maturity, and plant height is desirable. Traditional plant breeding is an important tool in developing new and improved commercial crops. This invention encompasses methods for producing a plant by crossing a first parent plant with a second parent plant wherein one or both of the parent plants is a transformed plant according to the invention displaying *Fusarium* resistance as described herein.

Plant breeding techniques known in the art and used in a plant breeding program include, but are not limited to, recurrent selection, bulk selection, mass selection, backcrossing, pedigree breeding, open pollination breeding, restriction fragment length polymorphism enhanced selection, genetic marker enhanced selection, doubled haploids, and transformation. Often combinations of these techniques are used.

The development of hybrids in a plant breeding program requires, in general, the development of homozygous inbred lines, the crossing of these lines, and the evaluation of the crosses. There are many analytical methods available to evaluate the result of a cross. The oldest and most traditional method of analysis is the observation of phenotypic traits. Alternatively, the genotype of a plant can be examined.

A genetic trait which has been engineered into a particular plant using transformation techniques can be moved into another line using traditional breeding techniques that are well known in the plant breeding arts. For example, a backcrossing approach is commonly used to move a transgene from a transformed maize plant to an elite inbred line, and the resulting progeny would then comprise the transgene (s). Also, if an inbred line was used for the transformation, then the transgenic plants could be crossed to a different inbred in order to produce a transgenic hybrid plant. As used herein, "crossing" can refer to a simple X by Y cross, or the process of backcrossing, depending on the context.

The development of a hybrid in a plant breeding program involves three steps: (1) the selection of plants from various germplasm pools for initial breeding crosses; (2) the selfing of the selected plants from the breeding crosses for several generations to produce a series of inbred lines, which, while different from each other, breed true and are highly uniform; and (3) crossing the selected inbred lines with different inbred lines to produce the hybrids. During the inbreeding process, the vigor of the lines decreases. Vigor is restored when two different inbred lines are crossed to produce the hybrid. An important consequence of the homozygosity and homogeneity of the inbred lines is that the hybrid created by crossing a defined pair of inbreds will always be the same. Once the inbreds that give a superior hybrid have been identified, the hybrid seed can be reproduced indefinitely as long as the homogeneity of the inbred parents is maintained.

Transgenic plants of the present invention may be used to produce, e.g., a single cross hybrid, a three-way hybrid or a double cross hybrid. A single cross hybrid is produced when two inbred lines are crossed to produce the F1 progeny. A double cross hybrid is produced from four inbred lines crossed in pairs (A×B and C×D) and then the two F1 hybrids are crossed again (A×B)×(C×D). A three-way cross hybrid is produced from three inbred lines where two of the inbred lines are crossed (A×B) and then the resulting F1 hybrid is crossed with the third inbred (A×B)×C. Much of the hybrid vigor and uniformity exhibited by F1 hybrids is lost in the next generation (F2). Consequently, seed produced by hybrids is consumed rather than planted.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims. Thus, many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims.

The following examples are offered by way of illustration and not by way of limitation.

Example 1

Five *Arabidopsis* Homozygous Mutants that are Infected by *P. sojae*.

We observed that single cells of the *Arabidopsis* mutant, pen1-1, but not that of its progenitor ecotype, Columbia, are penetrated by *P. sojae*. This observation suggested that the first line of defense in *Arabidopsis* against the pathogen is lost in this mutant. We used the chemical mutagen, ethyl methane sulfonate (EMS), to generate 3,556 EMS-induced mutant plants in pen1-1. Then we have screened over 3,000 M2 families developed from these mutants for possible loss of *Fusarium* resistance in 24-well microtiter plates as follows. Seedling were grown in water for 10 days and then inoculated with *P. sojae* zoospores for 48 hours in wells of microtiter plates. Thereafter, dead cells of inoculated seedlings were stained with trypan blue dye (Koch and Slusarenko 1990) and identified by conducting light microscopy. We identified 30 putative *P. sojae* susceptible mutants. We tentatively named these putative mutants (putants) pss1 (*P. sojae* susceptible) through pss30.

We selected Niederzenz to cross withpss mutants to generate materials that segregate for the Pss genes, because this ecotype is immune to *P. sojae*. We generated a global map of SSLP and CAPS markers that are polymorphic between Columbia and Niederzenz. We sequenced the Niederzenz genome by applying high through-put Solexa (Illumina, Inc., San Diego) sequencing technology and developed a sequence-based polymorphic (SBP) markers technology to fill out the marker-poor regions of the genome developed earlier using SSLP and CAPS markers (Sahu et al. 2012). We developed SBP markers for saturating the Pss1 region with molecular markers.

We investigated map locations of three additional putative Pss genes, Pss6, Pss26 and Pss30. By conducting bulk-segregant analysis (Michelmore et al. 1991) we have shown that none of the putative Pss6, Pss26 and Pss30 genes mapped to the Pss1 locus. Pss30 was mapped to the south arm of Chromosome 5.

Pss6 is tentatively mapped to the Chromosome 4. Additional SBP markers are being generated to map this gene.

We inoculated all available 26 pss mutants and discovered that pss21 is also infected by *F. virguliforme*. Earlier we have shown through T-DNA tagged mutant analyses that the GRP1 gene encoding a glycine-rich protein is the Pss1 gene. We investigated if Pss21 is the Pss1 gene. We sequence the GRP1 gene from the pss21 mutant and observed that it did not contain any mutation. Therefore, we concluded that Pss21 is most likely different from Pss1 and there are most likely at least two mechanisms conferring immunity of *Arabidopsis* against the fungal pathogen, *F. virguliforme* that causes sudden death syndrome in soybean. Pss6 and pss30 mutants are immune to *F. virguliforme*. Therefore, Pss21 is most unlikely mapped to either of Pss6 and Pss30 loci. Thus, we have so far identified four genetic loci that are involved in immunity of *Arabidopsis* against *P. sojae*; they are: Pss1, Pss6, Pss21 and Pss30.

Nonhost resistance mechanism of *Arabidopsis* makes this model plant immune to all soybean pathogens. Therefore, transfer of the nonhost resistance mechanism from *Arabidopsis* to soybean is expected to create broad-spectrum resistance against most pathogens in soybean. In order to achieve this goal, we created *Arabidopsis* mutants, some of which are infected by the soybean pathogen *Phytophthora sojae*.

We have shown that the *Arabidopsis* Pss21 (*Phytophthora sojae* susceptible 21) and Pss25 genes are required for immunity of *Arabidopsis* to two soybean pathogens, root rot pathogen *P. sojae* and the SDS pathogen, *F. virguliforme*. Thus, transfer of this gene is expected to confer immunity to both soybean pathogens.

FIG. 1. *Arabidopsis* pss1 and pss25 mutants are susceptible to the *Fusarium virguliforme* Mont-1 isolate. Screening of a large mutant *Arabidopsis* population generated by treatment of the germinating seeds of the pen1-1 mutant with the chemical mutagen, ethyl methane sulfonate, resulted in isolation of 30 putative mutants that were susceptible to *Phytophthora sojae*, and were termed as *Phytophthora sojae* susceptible (pss) mutants. pss1, pss21 and pss25 (pss1 and pss25 are shown in this picture with arrows) were also shown to be susceptible to the SDS pathogen *Fusarium virguliforme*. Col-0 is the ecotype used in generating eight mutants including pen1-1 shown in this picture. These eight *Arabidopsis* mutants are compromised in resistance against *Arabidopsis* pathogens and pen mutations are susceptible to some nonpathogens of *Arabidopsis*. Note that pss1 and pss25 (shown by arrows) are highly susceptible to *F. virguliforme* and by seven days following inoculation, the leaves were completely colonized by the soybean pathogen. These results are consistent among three replications (one shown here). Pss1, Pss21 and Pss25 genes, mutated in pss1 and pss25 mutants, respectively, could provide durable resistance against the *F. virguliforme* isolates.

Example 2

According to the invention, one can create SDS resistant soybean cultivars by transferring *Arabidopsis* nonhost resistance genes Pss21 and Pss25 genes to soybean through transformation procedure. Earlier we have shown that pss21 and pss25 mutants lacking functional Pss21 and Pss25 genes are susceptible to both *Phytophthora sojae* and *F. virguliforme*. This observation suggested that functional Pss21 and Pss25 genes are essential for resistance of *Arabidopsis* to both pathogens. Since functional Pss21 and Pss25 genes are required for resistance of *Arabidopsis* against the two soybean pathogens, *P. sojae* and *F. virguliforme*, transfer of these two genes to soybean by transformation procedure will enhance resistance of soybean against both pathogens.

Identification of Arbidopsis Pss21 and Pss25 Genes that Confer Broad Spectrum Resistance to Soybean SDS Pathogen *Fusarium virguliforme* and Root Rot Pathogen *Phytophthora sojae*

Map-based or positional cloning of a gene is accomplished based on map position of the gene on the chromosomes. In *Arabidopsis*, this can be accomplished as follows: (i) first generate a high-resolution and high-density molecular map of the gene of interest, (ii) identify the candidate genes based on comparison of sequences of the mutant with that of the wild-type, (iii) identify the T-DNA-induced mutant lines for the candidate genes; (iv) analyze T-DNA mutants to identify the gene, and (v) isolate multiple loss of function mutants to identify a target gene.

(i) Develop High-Resolution and High-Density Molecular Maps of Pss21 and Pss25 Genes that Confer Nonhost Resistance Against *Phytophthora sojae* and *Fusarium virguliforme*.

Pss21 and pss25 mutants identified by screening EMS mutants with the soybean pathogen *P. sojae* were subsequently shown to be susceptible also to another soybean pathogen *F. virguliforme*. Both mutants were crossed to the wild-type Niederzenz and several $F_1$s were obtained from each cross. We generated $F_{2:3}$ segregating populations for each mutant gene inoculated with *P. sojae* to map the two Pss genes. $F_{2:3}$ families descended from crosses of pss21 and pss25 mutants with Niederzenz were infected with *P. sojae* isolates, CC5C and R25. Susceptible families were identified from this screening. DNA samples were bulked from at least 10 susceptible $F_{2:3}$ families descended from each cross of Niederzenz with either pss21 or pss25 mutant, and used in identifying molecular markers that are linked to these two resistance genes. By applying this bulked DNA from susceptible families we tentatively map Pss21 and Pss25 to chromosomes 5 and 4, respectively. The molecular map of the two genetic loci is presented in FIGS. 2 and 3. Both genes were mapped to small genomic regions. Pss21 is mapped on Chromosome 5 and tightly linked to marker M555 (FIG. 2). Pss25 is mapped on chromosome 4 and tightly linked to marker SBP 15.06 (FIG. 3). Pss21 mapped to Chromosome 5 and Pss25 to Chromosome 4.

FIG. 2. Molecular mapping of the Pss21 locus. A) Bulked-segregation analyses of the Pss21 locus: Lane 1, a bulk DNA sample of 14 $F_{2:3}$ susceptible families carrying the Pss21 gene; Lane 2, ecotype Columbia (Col-0), parent of the pss mutants; Lane 3, Niederzenz (Nd-0); and Lane 4, DNA of Col-0 and Nd-0 in equal proportion. Ten $F_{2:3}$ susceptible families carrying mutation in the Pss21 gene were evaluated for molecular markers MBK-5 and LUGSSLP151 (see genetic map positions of these two loci on the south arm of chromosome 5 in C on the right). Note MBK-5 showed only Col-0 phenotype; whereas, LUGSSLP151 showed Nd-0 type. Thus, Pss21 is linked to MBK-5 on south arm of chromosome 5 because pss21 mutant was developed by mutating the progenitor ecoptype, Col-0, and the phenotype of the bulked pss21 pool of 14 families matched the Col-0 phenotype. B) Co-segregation of pss21 with MBK-5 and M555 markers. Ten susceptible $F_{2:3}$ susceptible families carrying the mutant allele, pss1, of the Pss21 gene were evaluated for molecular markers MBK-5 and M555. Note that M555 showed Col-0-type phenotype for all susceptible $F_{2:3}$ families. On the other hand, MBK-5 showed heterozygosity for two susceptible families. Therefore, Pss21 is in between MBK-5 and the telomere and M555 is tightly linked to Pss21. C) Molecular map of the south arm Chromosome 5 including the Pss21 region (box) is shown.

FIG. 3. Molecular mapping of the Pss25 locus. A) Bulked-segregation analyses of the Pss25 locus: Lane 1, bulked DNA samples of 9 $F_{2:3}$ susceptible families carrying the Pss25 allele; Lane 2, bulked DNA sample of 12 $F_{2:3}$ susceptible families carrying the pss25 allele; Lane 3, a bulk DNA sample of 7 $F_{2:3}$ susceptible families carrying the pss25 allele; Lane 4, ecotype Columbia (Col-0), parent of thepss mutants; Lane 5, Niederzenz (Nd-0); and Lane 6, DNA of Col-0 and Nd in equal proportion. Note that the susceptible bulked DNA samples showed the Col-0 phenotype for SBP5_14.5 and NGA1139 markers; therefore, Pss25 is linked to these two markers. B) Co-segregation of pss25 with SBP4_12.5, SBP4_14.0, SBP4_15.06, NGA1139 and NGA1107 markers. Fifteen $F_{2:3}$ susceptible families carrying mutation in the Pss25 gene were evaluated for molecular markers SBP4_12.5, SBP4_14.0, SBP5_15.06, NGA1139 and NGA1107 (see genetic map positions of these two loci on the south arm of chromosome 4 in C). Note that SBP5_15.06 showed Col-0-type phenotype for all susceptible $F_{2:3}$ families. On the other hand SBP4_12.5, SBP4_14.0, and NGA1107 showed heterozygosity. NGA1139 showed heterozygosity for two susceptible families. Therefore, Pss25 is in between SBP4_15.06 and NGA1139 and SBP4_15.06 is tightly linked to Pss25. Fifteen susceptible $F_{2:3}$ susceptible families carrying the Pss25 gene were evaluated for molecular markers SBP4_12.5, SBP4_14.0, SBP4_15.06, NGA1139 and NGA1137. C) Molecular map of the south arm chromosome 4 including the Pss25 region (box).

(ii) Identify the Candidate Genes Based on Comparison of Sequences of the Mutant with that of the Wild-Type.

To facilitate cloning of Pss21 and Pss25, individual $F_{2:3}$ families showing the susceptible phenotype for each mutant gene were pooled and their bulked genomic DNA was used to prepare an genomic library for sequencing a high-throughput next generation sequencing (NGS) instrument at the ISU DNA facility. Basic steps to define the causal mutation were (1) mapping of sequence reads to the reference Col-0 genome which is currently available to the research community on the web (http://phytozome.jgi.doe-.gov/pz/portal.html), (2) we looked for polymorphic sequences for single nucleotide (SNP) between a mutant with the Col-0 genome sequence for the region, into which a Pss gene was mapped. By comparing sequences of the Pss21 region of the bulked susceptible $F_{2:3}$ families homozygous for the pss21 allele with that of the ecotype Col-0, we identified six SNPs that can alter composition of six proteins encoded by six genes of the Pss21 region (Table 1).

TABLE 1 pss21 identified non-synonymous SNPs, their position and gene identification.

| Position | Base | Changed to | Gene Locus | Candidate Pss21 Gene |
|---|---|---|---|---|
| 25,950,267 | C | T | At5g64940 | ABC1-LIKE PROTEIN 1 |
| 25,741,399 | C | T | At5g64380 | Inositol family protein |
| 26,402,837 | C | T | At5g66020 | IBS2 |

TABLE 1-continued pss21 identified non-synonymous SNPs,
their position and gene identification.

| Position | Base | Changed to | Gene Locus | Candidate Pss21 Gene |
|---|---|---|---|---|
| 26,504,721 | C | T | At5g66350 | RING finger-like zinc finger family |
| 26,123,694 | C | T | At5g65380 | Antiporter activity |
| 26,796,808 | C | T | At5g67150 | Transferase activity |

By comparing the sequences of the Pss25 genomic region of the bulked susceptible $F_{2:3}$ families homozygous for the pss25 allele with that of the wild-type ecotype, we identified only one mutation in the At4g36870 gene that can alter the function of the BEL family of homodeodomain protein (BLH2) encoded by this gene. Therefore, this is the candidate Pss25 gene.

(iii) Identify the T-DNA-Induced Mutant Lines for the Candidate Genes of the Pss21 Region.

In order to identify the Pss21 from the six candidate genes shown in Table 1, we gathered T-DNA tagged lines that contain knockout mutations for each of these six genes. T-DNA (transfer DNA) is a part of a plasmid of the *Agrobacterium tumefaciens* is use to transform plants. *Agrobacterium* transfers T-DNA into plant genomes and wherever it gets inserted, it causes mutation. We selected those *Arabidopsis* lines that carry T-DNA molecules in any of the six genes of interest. We gathered multiple T-DNA induced for each of the six genes (Table 2).

TABLE 2

Salk T-DNA induced mutant lines for candidate pss21 genes.

| Gene Locus | T-DNA insertion mutant |
|---|---|
| AT5G64940 | 006766 (*Promoter), 045739C (exon), 080442 (exon) |
| AT5G64380 | 106586 (exon), 053799 (exon), 061797 (exon) |
| AT5g66020 | 021488 (promoter), 086490 (promoter), 031243 (promoter) |
| AT5G66350 | 044983 (exon), 095949 (promoter), 145181 (exon) |
| AT5G65380 | 067673 (exon), 067673 (exon), 067674 (exon) |
| AT5G67150 | 054444 (exon), 055884 (exon), 046118 (exon) |

*Location of T-DNA insertions in genes are shown in parenthesis.

In order to confirm if At4g36870 is the Pss25 gene, we gathered T-DNA insertion mutants for this gene from the *Arabidopsis Biological Resource* Center (ABRC). Progenies of each of the T-DNA insertion mutants for the At4g36870 gene were inoculated with *P. sojae* spores.

(iv) Isolate Multiple Loss of Function Mutants to Identify a Target Gene.

Progenies of each the T-DNA-insertion mutants (Table 2) for the six candidate Pss21 genes were inoculated with *P. sojae* spores to determine which one are pss21 mutants. Only one class of three independent T-DNA-induced mutants generated from insertion in the At5g64940 gene was susceptible to *P. sojae* (FIG. 4) confirming that Pss21 encodes an ABC-like protein 1.

Figure 5A:
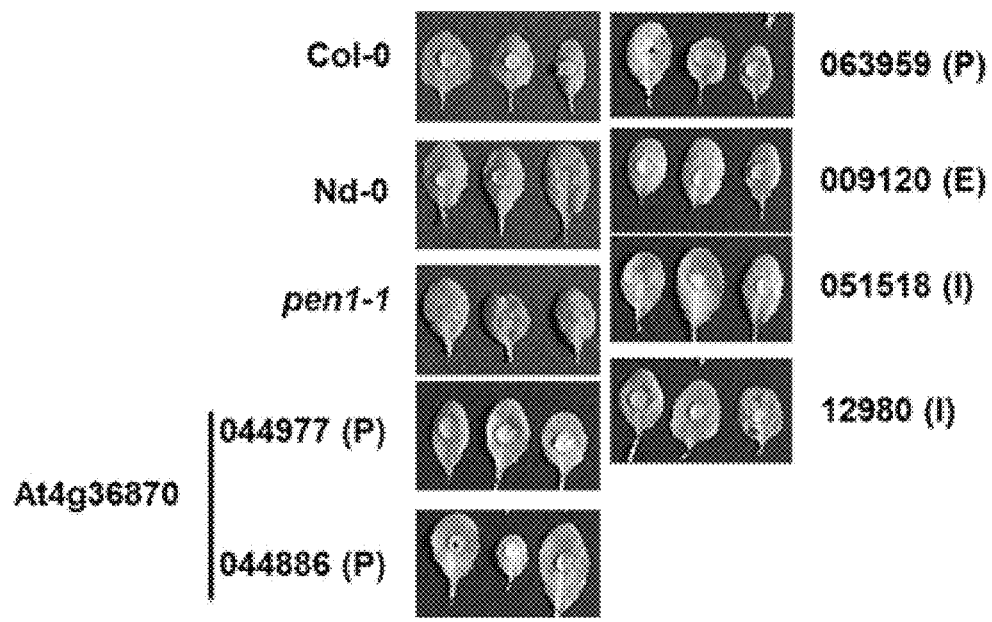
FIG. 5A-5B shows the phenotypes of *Arabidopsis* T-DNA insertion mutant of the candidate Pss25 gene At4g36870.
Figure 5B:
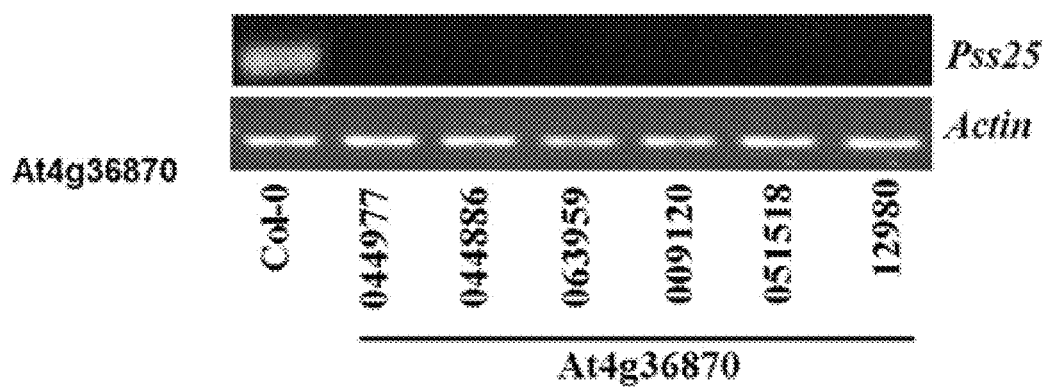

To confirm if At4g36870 is the Pss25, all six T-DNA insertion mutants for the gene were inoculated with and results are presented in *P. sojae* (FIG. 5). All six mutants were susceptible to *P. sojae*. Therefore, At4g36870 encoding a BEL family of homodeodomain protein (BLH2) is the Pss25 gene.

Figure 4A:
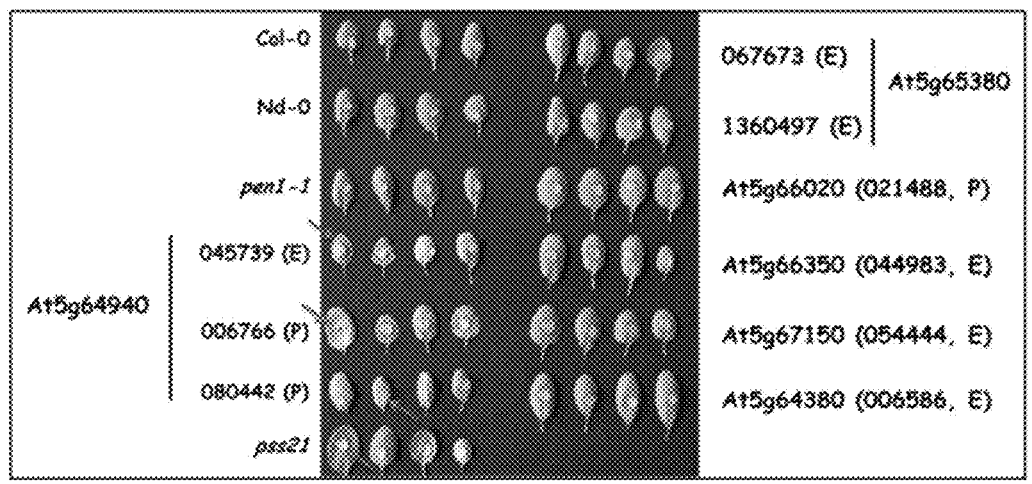
FIG. 4A-4B shows the phenotypes of *Arabidopsis* mutant plants with the T-DNA insertion mutations in the candidate Pss21 genes.
Figure 4B:
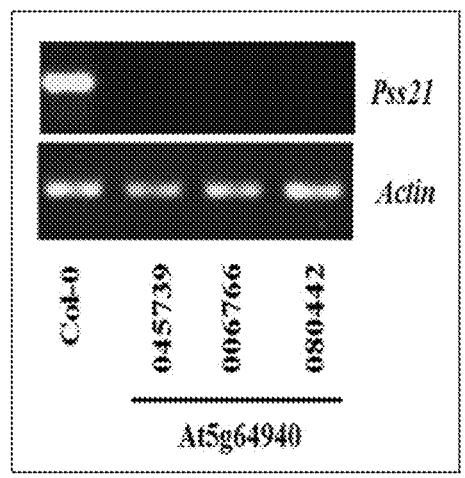

FIG. 4. Phenotypes of *Arabidopsis* mutant plants with the T-DNA insertion mutations in the candidate Pss21 genes. A) Three-week-old *Arabidopsis* seedlings of Col-0, Nd-0, pen1-1, pss21, T-DNA knock-out lines of candidate Pss21 genes (At5g64940, At5g65380, At5g66020, At5g66350, At5g67150 and At5g64380) were inoculated with *P. sojae* spores at a concentration of $3 \times 10^5$ spores/ml. Symptoms were evaluated after 48 hour post inoculation. P, T-DNA insertions in promoters; E, T-DNA insertions in exons. B) Confirmation of knockout of Pss21 gene in T-DNA lines of Pss21 by RT-PCR. RNA was isolated from wild-type (Col-0) and *P. sojae* susceptible T-DNA mutant lines of Pss21 and the expression of Pss21 gene was monitored by RT-PCR. Actin gene is expressed in both Col-0 and Pss21 T-DNA mutant lines (045739, 006766 and 080442) suggesting that Pss1 transcripts are absent in Pss21 T-DNA mutant lines.

FIG. 5. Phenotypes of *Arabidopsis* T-DNA insertion mutant of the candidate Pss25 gene At4g36870. A) Three-week-old *Arabidopsis* seedlings of Col-0, Nd-0, pen1-1 and T-DNA knock-out lines (044977, 044886, 063959, 009120, 051518 and 12980) of candidate Pss25 gene (At4g36870) were inoculated with *P. sojae* spores at a concentration of $3 \times 10^5$ spores/ml. Symptoms were evaluated after 48 hour post inoculation. P, T-DNA insertions in promoters; E, T-DNA insertions in exons and I, T-DNA insertions in exons. B) Confirmation of knockout of Pss25 gene in T-DNA lines of Pss25 by RT-PCR. RNA was isolated from wild-type (Col-0) and *P. sojae* susceptible T-DNA mutant lines of Pss21 and the expression of Pss21 gene was monitored by RT-PCR. Actin gene is expressed in both Col-0 and Pss25 T-DNA mutant lines suggesting that Pss25 transcripts are absent in T-DNA mutant lines.

Example 3

Identification of Pss6 Encoding a Vesicle-Associated Membrane Protein 724.

A similar map-based cloning approach in cloning Pss6 that confers resistance of *Arabidopsis* to both *P. sojae* and *F. virguliforme*. The gene was mapped to Chromosome 6 and four candidate Pss6 genes were identified from comparison genome sequence of pss6 mutant with Col-0 reference genome sequence. They are: At5g15780, At4g16680, At4g15130, and At4g17100. Analysis of T-DNA insertion mutants established that At4g15130 encoding a vesicle-associated membrane protein 724 is the Pss6 gene.

Figure 6A:
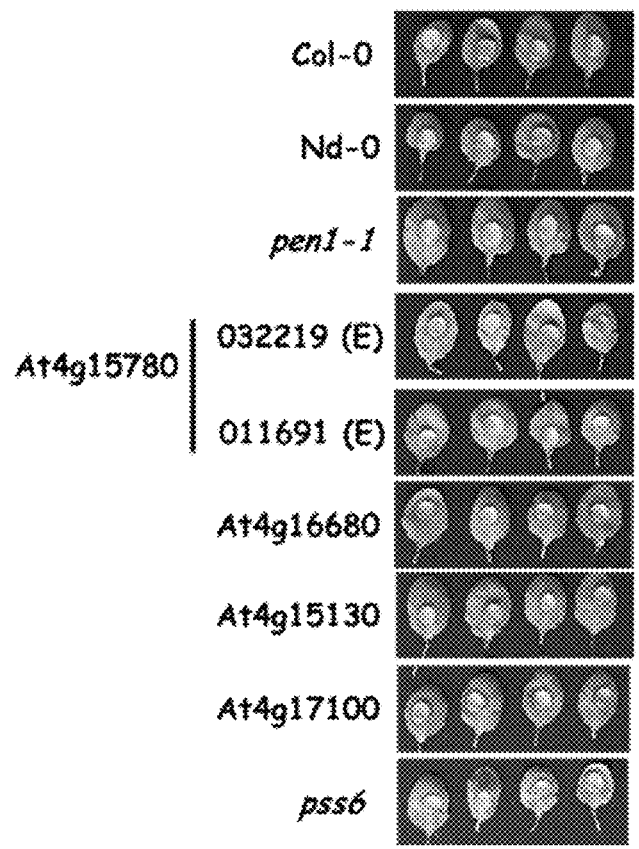
FIG. 6A-6B shows the phenotypes of *Arabidopsis* mutant plants with T-DNA insertions in candidate Pss6 genes.
Figure 6B:
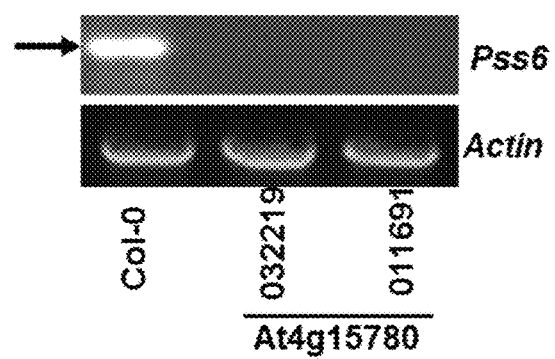
Figure 7A:
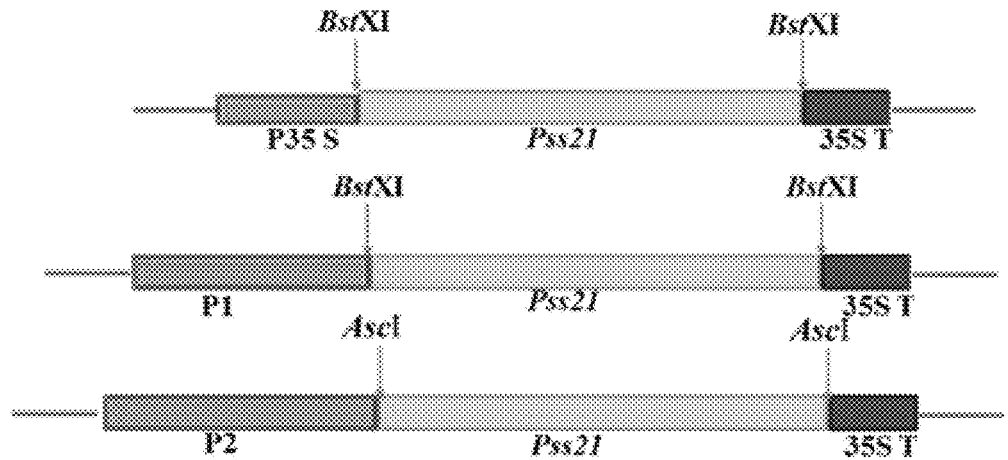
FIGS. 7A-7F show the expression cassettes and cloning of Pss21, Pss25 and Pss6 genes in binary vector for soybean transformation.
Figure 7B:
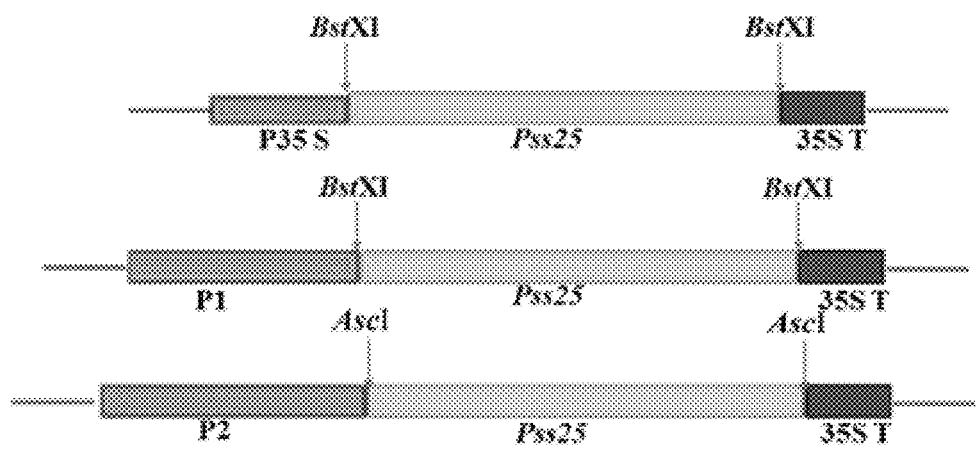
Figure 7C:
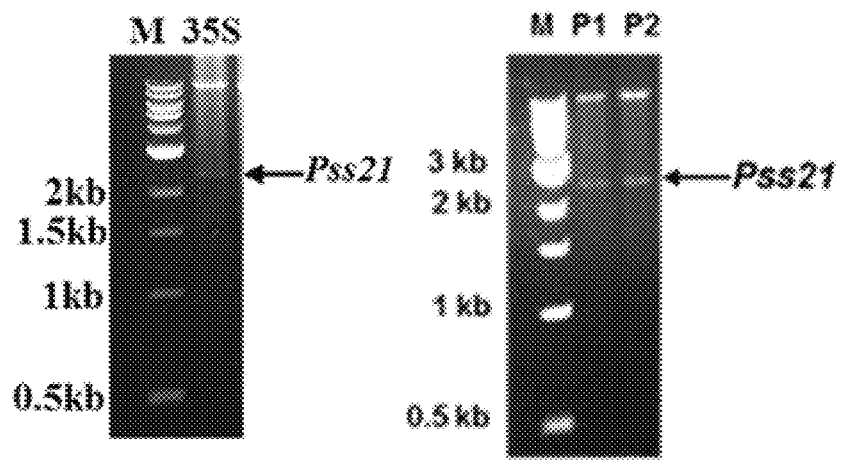
Figure 7D:
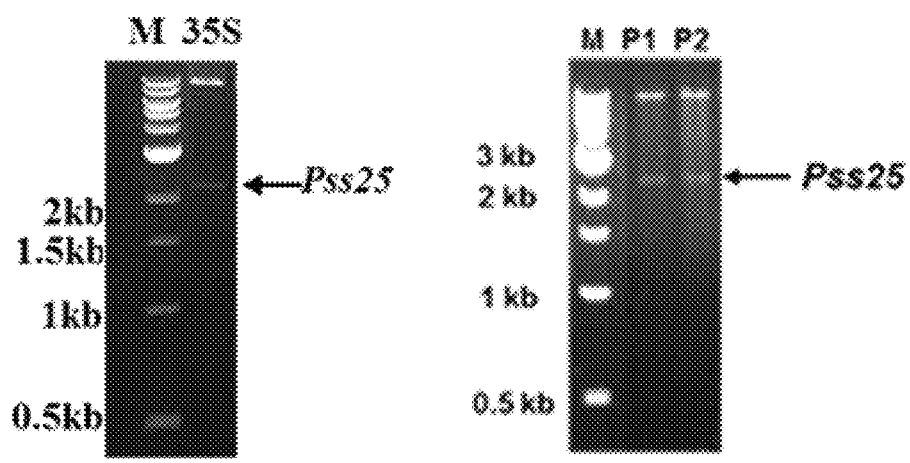
Figure 7E:
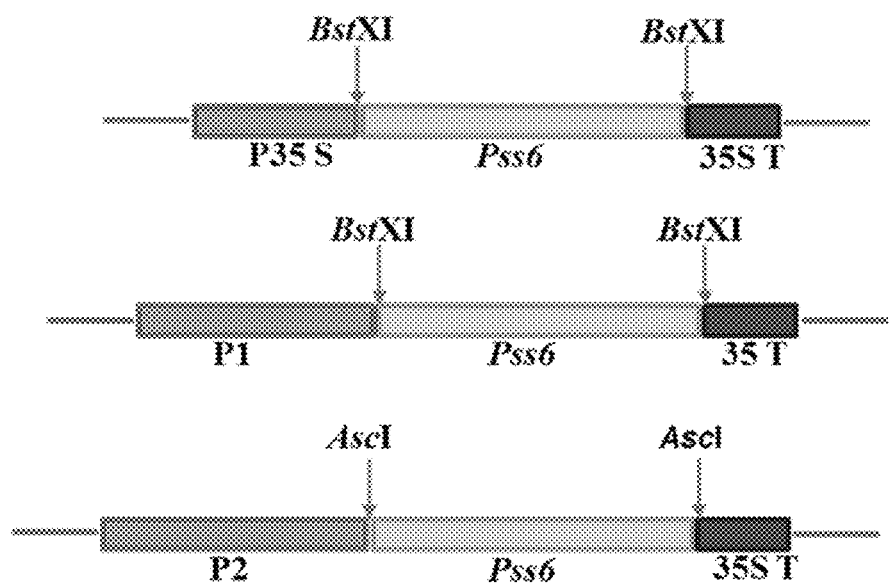
Figure 7F:
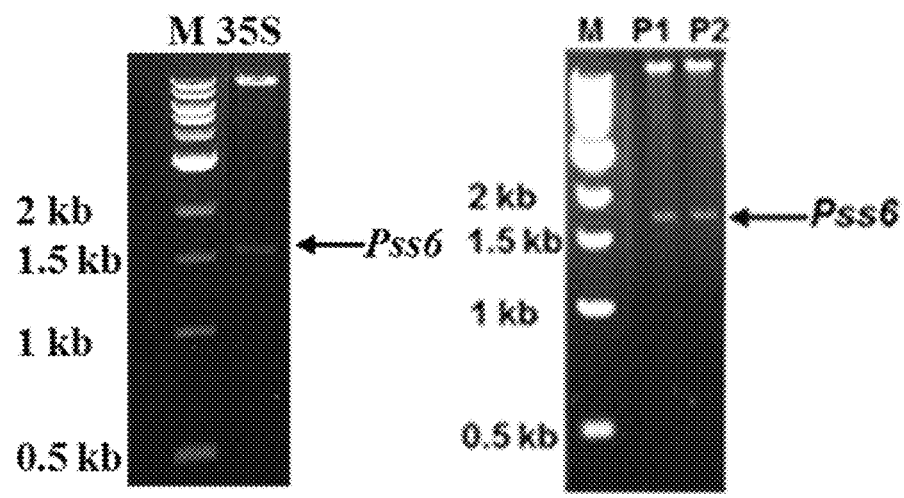

FIG. 6. Phenotypes of *Arabidopsis* mutant plants with T-DNA insertions in candidate Pss6 genes. A) Three-week-old *Arabidopsis* seedlings of Col-0, Nd-0, pen1-1, pss6, T-DNA knock-out lines of candidate Pss6 genes (At4g15130, At4g15780, At4g17100 and At4g16680) were inoculated with *P. sojae* spores at a concentration of $3 \times 10^5$ spores/ml. Symptoms were evaluated after 48 hour post inoculation. E, T-DNA insertions in exons. B) Molecular characterization of T-DNA insertion pss6 mutants. RNA was isolated from wild-type (Col-0) and *P. sojae* susceptible T-DNA insertion mutant lines and the pression of Pss6 gene (At4g15780) was monitored by RT-PCR. Actin gene is expressed in both Col-0 and Pss6 T-DNA insertion mutant lines (032219 and 011691) However, Pss6-specific transcripts (shown by an arrow) are absent in Pss6 T-DNA mutant lines.

Example 4

Generation of Transgenic Soybean Lines for Pss6, Pss21 and Pss25 Genes:

In order to determine if Pss6, Pss21 and Pss25 genes can confer immunity against *F. virguliforme* and *P. sojae* in transgenic soybean plants, we started to create transgenic soybean lines carrying these three genes under the regulation of three promoters. Each of the Pss6, Pss21 and Pss25 genes was PCR amplified from reverse transcribed *Arabidopsis* ecotype Col-0 leaf mRNAs and cloned initially in to pGEMT vector and sequenced to confirm the identity of the genes. Each of these genes were then cloned into a binary vector to express in soybean under the control of three promoters: (i) Promoter 1, promoter of the soybean Glyma18g47390 gene that becomes active following *F. virguliforme* infection; (ii) Promoter 2, promoter of the soybean Glyma10g31210 gene that is active in roots and induced following pathogen infection, and (iii) the CaMV 35S promoter. The nine gene constructs were transformed into *Agrobacterium tumefaciens* EHA101 for development of stable transgenic soybean lines. Transformed *A. tumefaciens* isolates carrying the nine gene constructs were verified for the individual Pss-fusion genes by separating restriction enzyme digestion products on an agarorse gel (FIG. 7) and provided to the Plant Transformation Facility (PTF), located at Iowa State University for generating transgenic soybean. A major activity in the past several months has been growing of transformants in greenhouse to collect the Ri seeds. Table 3 includes the transformants, for most of which Ri seeds have been harvested. We failed to generate transgenic soybean plants for fusion genes, 35S-Pss6 (ST233), Prom1-Pss21 (ST304) and 35S-Pss25 (ST322) in repeated trials. Both 35S and Prom 1 are active during transformation; and it is possible that Pss6, Pss21 and Pss25 proteins expressed in transformed cells could be toxic for regeneration of transgenic plants.

FIG. 7. The expression cassettes and cloning of Pss21, Pss25 and Pss6 genes in binary vector for soybean transformation. A, B and E: Constructs used for development of transgenic soybean for *Arabidopsis* nonhost genes Pss21, Pss25 and Pss6. C, D and F: Molecular characterization of the constructs carrying P35S, P1 and P2 promoters and Pss21, Pss25 and Pss6 genes. P35S, CaMV 35S promoter; P1, Promoter 1, infection inducible promoter; P2, infection-inducible and root-specific promoter; 35S T, CaMV 35S terminator; BstXI and AscI are restriction enzymes used for cloning of Pss21, Pss25 and Pss6 in pTF102 binary vector. M, 1 kb DNA ladder.

TABLE 3

Generation of transgenic soybean plants for Arabidopsis Pss6, Pss21 and Pss25 genes.

| Construct | R₀ Line | Growth Pattern | No. of R₁ Seed |
|---|---|---|---|
| Prom1-Pss6 | ST302-1 | Normal | 219 |
|  | ST302-7 | Normal | 60 |

TABLE 3-continued

Generation of transgenic soybean plants for Arabidopsis Pss6, Pss21 and Pss25 genes.

| Construct | R₀ Line | Growth Pattern | No. of R₁ Seed |
|---|---|---|---|
|  | ST302-8 | Normal | 28 |
|  | ST302-11 | Died |  |
| Prom2-Pss6 | ST303-11 | Normal | 100 |
|  | ST303-13 | Normal | 23 |
|  | ST303-9 | Stunted | Seeds not produced |
| 35S-Pss6 | ST323 | Failed | N/A |
| Prom1-Pss21 | ST304 | Failed | N/A |
| Prom2-Pss21 | ST305-1 | Normal | 187 |
|  | ST305-7a | Normal | 219 |
|  | ST305-7b | Normal | 341 |
|  | ST305-11 | Normal | 211 |
|  | ST305-17 | Normal | 64 |
| 35S-Pss21 | ST321-11 | Normal | 113 |
|  | ST321-6 | Stunted | 28 |
|  | ST321-2 | Normal | 142 |
|  | ST321-8 | Normal | 203 |
|  | ST321-10 | Normal | 144 |
|  | ST321-19 | Normal | 188 |
|  | ST321-18 | Stunted | 134 |
|  | ST321-20 | Normal | 154 |
|  | ST321-17 | Normal | 34 |
| Prom1-Pss25 | ST306-3 | Normal | 164 |
|  | ST306-4 | Normal | 289 |
|  | ST306-16 | Normal | 126 |
|  | ST306-11 | Normal | 140 |
|  | ST306-14 | Normal | 226 |
|  | ST306-8 | Normal | 49 |
| Prom2-Pss25 | ST307-3 | Normal | 174 |
|  | ST307-5 | Normal | 154 |
|  | ST307-12 | Normal | 22 |
|  | ST307-13 | Stunted | No seeds |
|  | ST307-14 | Normal | 283 |
|  | ST307-17 | Normal | 17 |
| 35S-Pss25 | ST322 | Failed | N/A |

Example 5

Figure 8:
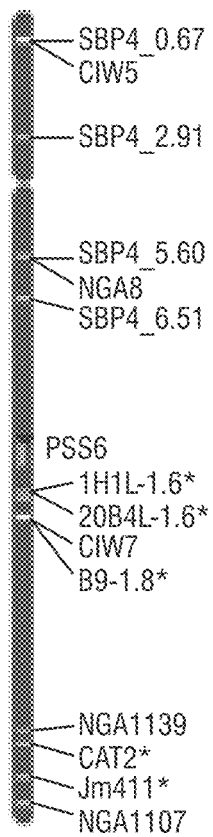

FIG. 8 is a map of chromosome 4 showing the location of pss 6.

The following sequence were obtained from World wide web at *Arabidopsis*.org NCBI accession numbers are also given as an alternative sequence source.

```
PSS 21

At5g64940 (GenBank: AY064044.1)

PSS21-At5g64940 Protein (SEQ ID NO: 4)
MATSSSSSSSLLLPNINFNSRQSPTITRSVSIAGIFLPRNRLSY

NHNLRIRTRLIRASKDDNVAVEDRDNAVKINGDYNGSARLNGNGSARKSVNGDFNGSA

RLNGNGSLVKYVNGSVTVETEEVTKKRKEEVRKKRVEDIGQEDAWFKNNTQQKQVEVSV

TPGGRWNRFKTYSTIQRTLEIWGFVVQFIFPRTWLSNKKFSYKGGMTEEKKVLRRKVL

AKWLKENILRLGPTFIKIGQQFSTRVDILPQEYVDQLSELQDQVPPFPSATALSIVEE

ELGGSVEDIFDRFDYEPIAAASLGQVHRARLKGQEVVLKVQRPGLKDLFDIDLKNLRV

IAEYLQKVDPKSDGAKRDWVAIYDECASVLYQEIDYTKEAANSELFANNFKDLEYVKV

PSIYWEYTTPQVLTMEYVPGIKINKIQALDQLGVDRKRLGRYAVESYLEQILSHGFFH
```

-continued

ADPHPGNIAVDDVNGGRLIFYDFGMMGSISPNIREGLLEAFYGVYEKDPDKVLQAMVQ

MGVLVPTGDLTAVRRTALFFLNSFEERLAAQRKEKEEIAAAEELGFKKPLSKEEKQEK

KKQRLAAIGEDLLAIAADQPFRFPATFTFVVRAFSVLDGIGKGLDPRFDITEIAKPYA

LELLRFREAGVEVVVKDLRKRWDRQSQAFYNLFRQADRVEKLAVVIERLEQGDLKLRV

RALESERAFQRVAAVQKTVGSAVAAGSLVNLATILYLNSIKTPATIAYTVCAFFSLQV

LIGIIKVKKFDQREKLITGTA

PSS21-At5g64940 Protein (SEQ ID NO: 3)

```
   1 gccaacaaac aacaagtctt caccttcttc ttcttcttct tcttcaaaat ctcttatacg
  61 caaataatcc ataagaaact agggtttaac ttgagatctc tcttccgaag tattaccatc
 121 aatggcgact tcttcttctt catcgtcgtc tctgctttta ccaaacatca atttcaactc
 181 aagacaatct ccaacaatca ctcgttccgt ttcaatcgcc gggatcttct tacccagaaa
 241 ccgattaagc tacaatcaca atctccggat tcgtacgaga ttaatcagag cttctaaaga
 301 cgataatgtc gctgttgaag atcgtgataa tgcagtgaag atcaacggtg attacaacgg
 361 aagtgcacgt ttaaacggta acggctctac gagaaaatcc gtcaacggag attttaacgg
 421 aagtgctcgt ttgaacggta acggtagttt ggtgaagtat gtgaacggaa gtgtaacggt
 481 ggaaacggag gaagtgacaa agaagagaaa agaagaagtg aggaagaaga gagtagaaga
 541 tattggtcaa gaggatgctt ggtttaagaa caacactcaa caaaaacaag ttgaggtttc
 601 tgttacacct ggtggtcgat ggaatagatt caagacttac tcaactattc aaagaacatt
 661 gaagatttgg ggttttattg tacagtttat tttcaggact tggttaagca ataaaaagtt
 721 ctcttataaa gggggaatga ctgaagagaa gaaggtttta agaaggaagg ttttggctaa
 781 gtgattgaaa gaaaacattt tgagattagg tcctacattt atcaaaattg gcaacagtt
 841 ctctactaga gtggatattc ttcctcaaga gtatgttgat caattgtcag aacttcagga
 901 tcaagttcct cctttccctt ctgctacagc tttatccatt gttgaagagg agcttggagg
 961 ttctgttgag gacattttcg accgttttga ttatgaacct atagctgcag ctagtcttgg
1021 gcaagttcac cgtgcaagac ttaagggtca agaggttgtc cttaaagtac agagacctgg
1081 tctgaaggat ctctttgata ttgaccttaa gaatttgagg gtgatcgctg agtatctcca
1141 aaaggtggac ccaaaatcag atggtgcaaa gagagattgg gttgcaatct atgatgaatg
1201 tgccagtgtt ttgtaccagg aaattgatta cacaaaagaa gcagctaatt cggagttgtt
1261 tgctaataac ttcaaagact tagagtatgt aaaagttcca tccatctact gggaatacac
1321 tacacctcag gtcctgacaa tggagtatgt ccctgggatt aagattaaca agatacaagc
1381 cttagatcag ttaggtgttg atcgaaaaag gctaggaaga tatgctgttg aatcttacct
1441 ggagcaaatc ttatctcatg gattcttcca cgccgaccct caccctggga atatagcagt
1501 tgatgatgtc aatgacaggc ggctgatatt ttacgacttt ggaatgatgg gaaatattag
1561 cccaaatatt agaagagatt tgttggaggc atttatggc gtctataaaa agatccaga
1621 taaggtcctt caagctatgg ttcaaatagg agtgcttgta ccaactggag atttgacggc
1681 agttagaaga acagcattgt tttttctcaa cagttttgaa gagcggcttg ctgcacaaag
1741 aaaggagaaa gaagaaatag cagcagcaga agagcttagg ttcaagaagc cactaagcaa
1801 ggaagaaaag caagagaaaa agaagcaaag gttggctgca atcggagaag acttattagc
1861 cattgcggct gatcagcctt tccggttccc cgccacattc acatttgttg ttagagcctt
1921 ttcagtattg gatggcatcg gcaaagatct tgacccccga tttgatataa cggagattac
1981 taaaccctat gctttggaat tgttgcggtt tcgagaagct agagtggaag ttgtagtaaa
```

```
2041 ggacctgaga aagagatggg acaggcaatc acaagcattc tacaatctat ttagacaagc 2101 ggatagagtt gaaaagctag ctgtagtcat tgaacgactt gagcaaggtg atttgaagct 2161 tagggtccga gcgctagagt ctgagagggc atttcaacgc gttgcagctg ttcaaaaaac 2221 agtaggaagt qctgttgctg caggaagttt agtcaatctc gcaacaattt tgtatctgaa 2281 ttctataaaa acacctgcaa ctatagcata tacagtatgt gctttcttca gcctccaagt 2341 tctaatcgga atcataaagg ttaagaagtt cgatcaacgg gaaaaactaa tcactggaac 2401 agcttaagaa cttgcttgaa gaaatgtatt aaagcttctt caatctccat aaacccttt 2461 gtgcatttca caggagtgtt aacaatttca ctggtctgca aataaaatta tcttatggaa 2521 gcttgagagg caagagatgg tcaactagtc aaaccaccac cactctctca tctctgtctt 2581 cttaaagttc gataataatt tttgagagg agactctggt tgttcatcaa cagagtggtc 2641 atgagccaca tgtattgctt gtgtatagag agatttagaa attaggaact ttttcgtata 2701 aatatactca ttgtactcag ctactcacta gactcatctc tgttttagta ataaaaaaaa 2761 aaaaaaaa
```

At4g15780 Pss6 Genbank BT014777

PSS6-At4g15780 Protein (SEQ ID NO: 2)
MGQESFIYSFVARGTMILAEYTEFTGNFPSIAAQCLQKLPSSSN

SKFTYNCDHHTFNFLVEDGYAYCVVAKDSLSKQISIAFLERVKADFKKRYGGGKASTA

IAKSLNKEFGPVMKEHMNYIVDHAEEIEKLIKVKAQVSEVKSIMLENIDKAIDRGENL

TVLTDKTENLRSQAQEYKKQGTQVRRKLWYQNMKIKLVVLGILLLLVLIIWISVCHGF

NCTD

PSS6-At4g15780 Protein (SEQ ID NO: 1)
```
  1 gtggcgactc aaatgggtca agaatcgttt atctatagct tcgtcgccag aggaactatg 61 atcctcgccg agtataccga attcacaggc aatttcccgt ctattgctgc tcagtgtctc 121 cagaagcttc cgtcctccag caacagcaag ttcacttaca actgcgatca ccatacctt 181 aatttccttg tcgaagatgg ctacgcatat tgtgttgtgg cgaaagattc tcttagcaag 241 caaatctcga tcgcatttct ggagcgtgtg aaagctgatt tcaagaagag atatggaggt 301 ggaaaagcaa gtacagctat cgccaaaagt ctcaacaagg agttcgggcc ggtgatgaag 361 gaacacatga attatattgt tgaccatgca gaggagattg aaaaactaat aaaagtcaag 421 gctcaggttt cagaagttaa agtataatg ttggagaata ttgacaaggc aatcgacaga 481 ggggaaaatc taacagttct tactgacaag accgagaatc tacgctctca ggcgcaggaa 541 tacaagaaac aagggacaca ggtgaggagg aaattgtggt accagaacat gaagataaaa 601 ctggtggttc ttgggatctt gctactactt gttctcataa tctggatatc ggtttgtcat 661 ggatttaatt gcacggattg aagacacaac aaatcactct acgtgatggt tagagactta 721 gagcttttgg cggagacagg cgacaaacag agacaaaagt cttcagtaga gagattagta 781 aagagagaga gaggggaaca aaatgataccc atatgtattg taaggttttg actttggatg 841 tt
```

Pss 25 (At4g36870) NC_003075.7

PSS25-At4g36870 Protein (SEQ ID NO: 6)
MGITKTSPNTTILLKTFHNNSMSQDYHHHHHHNQHQGGIFNFSN

GFDRSDSPNLTTQQKQEHQRVEMDEESSVAGGRIPVYESAGMLSEMFNFPGSSGGGRD

LDLGQSFRSNRQLLEEQHQNIPAMNATDSATATAAAMQLFLMNPPPPQQPPSPSSTTS

PRSHHNSSTLHMLLPSPSTNTTHHQNYTNHMSMHQLPHQHHQQISTWQSSPDHHHHHH

NSQTEIGTVHVENSGGHGGQGLSLSLSSSLEAAAKAEEYRNIYYGANSSNASPHHQYN

QFKTLLANSSQHHQVLNQFRSSPAASSSSMAAVNILRNSRYTTAAQELLEEFCSVGR

GFLKKNKLGNSSNPNTCGGDGGGSSPSSAGANKEHPPLSASDRIEHQRRKVKLLTMLE

EVDRRYNHYCEQMQMVVNSFDIVMGHGAALPYTALAQKAMSRHFRCLKDAVAAQLKQS

CELLGDKDAAGISSSGLTKGETPRLRLLEQSLRQNRAFHQMGMMEQEAWRPQRGLPER

SVNILRAWLFEHPLHPYPSDADHKLLARQTGLSRNQVSNWFINARVRLWKPMVEEMYQ

QESKEREREEELEENEEDQETKNSNDDKSTKSNNNESNFTAVRTTSQTPTTTAPDASD

ADAAVATGHRLRSNINAYENDASSLLLPSSYSNAAAPAAVSDDLNSRYGGSDAFSAVA

TCQQSVGGFDDADMDGVNVIRFGTNPTGDVSLTLGLRHAGNMPDKDASFCVREFGGF

PSS25-At4g36870 Protein (SEQ ID NO: 5)

```
   1 gtgggctaaa aagggtgacg aagaagaaag aagagtgacc tctctctcgc atattttct
  61 ttccgatata tatatctttt ataatatttg tgaattctga ataaactctt agtaagaaag
 121 aaaaggagag tccagaaaaa gaaagtgaga agagagaga gaaacgata cctaagctca
 181 attatcttct ctgcaacaaa ctccaaaggt attatcttct tatgctctct ctttgcatac
 241 atacatatat atagatacct acatatatat atctctatgt ctttgttcat catcagttat
 301 ataggtgatg tagatagatg gacaaaaaaa cagcgtaaga cctagtttct gacttacata
 361 tgttttaaat tctttgtctg aatcattaca ggatccaaga gagagagctc tggaacgata
 421 ttaacatata tcatgaagaa aaagattgaa gtattgatat gggaataact aaaacttctc
 481 ctaatactac aattctcttg aagacttttc acaataattc tatgtcccaa gattatcatc
 541 atcatcatca tcataatcaa caccaagaag gtatcttcaa cttctctaat ggattcgacc
 601 gatcagattc tcccaattta acaactcagc agaagcaaga gcatcaaagg gtagagatgg
 661 acgaggaatc ttcagtcgcc ggaggtaaga ttccggtcta cgaatcagcc ggtatgttat
 721 ccaaaatatt taatttcccc ggaagcagcg gtggaggaag agatctcgac ctcggccaat
 781 ctttccggtc aaataggcag ttgcttgagg agcaacatca gaatattcca gctatgaatg
 841 ctacggattc agccaccgcc accgcagccg ccatgtagtt attcttgatg aatccaccgc
 901 caccgcaaca accaccgtct ccgtcatcca aacttcccc aaagagccac acaattctt
 961 caactcttca catgttactt ccaagtccat ccaccaacac aactcaccat cagaactaca
1021 ctaatcatat gtctatgcat cagcttccac atcagcatca ccaacagata tcgacgtggc
1081 agtattctcc cgatcatcat catcatcatc acaacagcca aacggagatt gggaccgtcc
1141 acatggaaaa cagcggagga cacggaggac aaggcttgtc cttatctctc tcatcgtctt
1201 tagaaactgc agtaaaaacg gaagagtata gaaacattta ctacggagcc aattcttcta
1261 acccatcacc ttatcatcaa tacaatcaat tcaagactct tcttgctaat tcttctcaac
1321 atcaccatca agtattaaac caattccgat catctccggt tgcttattcc tcttccatgg
1381 cagcggtcaa tatcttaaga aactcgaggt acacaacggc cgcgcaagag ttgttggaag
1441 agttttgtag tgttggaaga ggattttga agaagaacaa acttgggaac agctcaaacc
1501 ctaatacttg cgatggtgat ggtggtggca gctctccttc gtcggccgga gcaaacaagg
1561 agcatcctcc tttatcggcg tctgatcgga ttgagcatca agaaggaaa gtgaaactac
1621 tcaccatgct tgaagaggta tgttcatatt aacttttaat attgattttg actttgtata
1681 tactctacag tgatattagt tcatacattt tacgtaaaat tgttttcgtt acatttcgat
1741 aagattcata aattgatcca agagttatga caaagaaaca agaaacctga tatgactgaa
1801 ttggtctttt gttttctcga ttaactactt atttttgatt attttggtag agtttgattg
```

-continued

```
1861 cgcaatccta ccatcatttg tttaaaatta aaattaattt aatcattttg ctcgtgtgac
1921 ggtcgtatta gaaagtatat tgaatatttt gatgcttagc gtttggtgga atcgattaat
1981 caaagaaaat gcattaaata attacgatta attatgtaat tggcgtttcc ttctccatat
2041 aagctactct ccagttacgt cctaaagcta acccttgacg ttacttattt gtttacccat
2101 aattgaatta tctactttt agttgacctt gctttttct cactagaaat aaatatttta
2161 gtttatgctc gaggatacga taaaatgtgc tgttggtagg attgcgcaaa cattgaagta
2221 tattctctgg tcaataattt gtctatataa tatcttattt tcttattttg tctcgtttaa
2281 aggtaactaa ttaatctcat taatttattt attagatgat gctcgtacac aagcataggt
2341 tcccgtgata aaatctacac taaataataa tcacgtgaac atataacaca acacacacga
2401 gttaacaata acattaatta aaaaaaaaaa gcaaatattg atatttatgg attgtataat
2461 gtatagtttt gtttcgttgg caggtggacc gacggtacaa ccattactgc gagcaaatgc
2521 agatggttgt gaactctttc gacatagtaa tgggccacgg tgcggcatta ccgtacaccg
2581 cattggctca aaaagctatg tcaagacatt ttagatgcct taaagatgca gttgcggctc
2641 agcttaagca gagttgcgaa cttcttgggg acaaagatgc agcgggaatc tcttattccg
2701 ggttaacaaa aggtgaaact ccgcgtttgc gtttgctaga gcaaagtttg cgtcagaacc
2761 gtgcgtttca tcaaatgggt atgatggaac aagaagcttg gcggccacaa cgcggtttgc
2821 ctgaacgctc cgtcaatata cttagagctt ggctcttcga acatttcctt cacccgtaag
2881 tcaatttttt ctttctttct cgttatttat taattattat agagaaactg aattttgaaa
2941 aaagctgaga aaaagtattt attttctcgt tatttcacct ctactttctt tagtactatg
3001 tctctagaat tttgctattt tattgttaac gagagtgaac gaaaaaatgg aaataaagca
3061 aaagagtagt gtttttgtac tattttcacc tctctgacaa attgctttaa gagtaaaaca
3121 aaacaaaaaa agccaagtaa aaaaaaaaaa actggatcga tgatatgtaa tcatcaactt
3181 ttcttttgtc tgttagattc tcacgccctt gttaggaaaa agtctgtact ttttcttgcg
3241 tctacttgat tgtattgtat atagtgaaaa gataaagaaa ataaattaca ttgagtttat
3301 tagggcaaag atagagagtg atgtcatttt ctggtctctt tctcaggtat ccaagtgatg
3361 cagataaaca cctattggct cgacagactg gtttatccag aaatcaggtc agtctacata
3421 tatacatata gccaacgata taatgaaatt taaaatctcc atgaatcaaa tacatatgcc
3481 tctacttcac caagttgtgt tagctgagta tactcttaat cagacaatca aatgaccaca
3541 gtctggatta cgaattctta accgcgtgtt ttaaagattt gttttaaacc catcattcta
3601 tgtttataaa taaactccac aatagtacac agttatatat ataactacaa tattaattta
3661 tcacccaaac ccatttcata attttcataa acatatacat gcttgttata aacatcaaat
3721 aataaatact agtagttact caaaacgaat ttgactaagc caaaattatt tgacaccatg
3781 tacgagtaca ctaactagta gcctgagatg actctattgc atggttttg tttcttatct
3841 ttatttggtt tgtgatatga cagaggaaca ccatgtgttt tgccttccac tcaccattag
3901 cttttcttgg gattcgtctt taaattatta tagcatattt atatatacaa aaacatagga
3961 gagagagaaa gagatcgaca ttaaagacgc aaaagggtcc attttcctc aagtacatca
4021 aagtttgcag ctttcaattg tcccaaagaa accctcaatt tcttgtatcc ctacattaaa
4081 taaccaaatg acaaataaac aaaaagagcc ctcaattta tttcgatatt ataatgattc
4141 aactagtgaa aattttgtct cttttattca ggtatcaaat tggttcataa atgctagggt
4201 tcgtttatgg aaaccaatgg tggaagaaat gtaccaacaa gaatcaaaag aaagagaaag
```

-continued

```
4261 agaagaggaa ttagaagaga acgaagaaga tcaagaaaca aaaaacagca acgacgacaa 4321 gagcacaaaa tccaacaaca atgaaagcaa cttcactgcc gttcggacca cttcacaaac 4381 tccaacgaca accgcaccac acgcatcaga cgcagacgca gcagtagcga caggccaccg 4441 tctaagatcc aacattaatg cttacgaaaa gacgcttcaa tcacttctac tcccttcctc 4501 ttattccaac gccgccgctc ctgccgctgt ttctacgaca ttgaattctc gttacggtgg 4561 ctcagacgcg ttttccgccg ttgccacgtg tcaacaaagt gtaggtgggt cgatgatgc 4621 tgacatggat ggtgttaacg ttataaggtt tggacaaaca cctactggtg acgtgtctct 4681 cacgcttggt ttacgccacg ctggaaacat gcctgacaaa gacgcttctt tctgcgttag 4741 agagtttggg ggttttagt ttgcttttgt cactccattt aattaattaa ttatagtttc 4801 cattcttact tattttaatt ttaaaatcta tttttgtctc ttaaaatcaa aacaatacat 4861 tagtctagcc ctcctctgct tttttttttc tatctcgtgaa agagaagaaa acgatacgta 4921 aatcccttcg aaaactaatg acgttgtac gacttattgta tttcat
```

---

What is claimed is:

1. A modified plant with improved *Fusarium* and *Phytophthora* tolerance compared to the *Fusarium* and *Phytophthora* tolerance of a corresponding plant with no such modification; said modified plant having a heterologous nucleotide sequence comprising a non host resistance nucleic acid sequence from *Arabidopsis*, said non host resistance nucleic acid sequence is one or more of the following: SEQ ID NOs: 1, 3, or 5 encoding one or more proteins selected from the group consisting of: SEQ ID NOs: 2, 4, and 6, respectively.

2. A method for conferring or improving *Fusarium* resistance in a plant, said method comprising:
transforming said plant with a nucleic acid molecule comprising a heterologous sequence operably linked to a promoter that induces transcription of said heterologous sequence in a plant cell; and
regenerating stably transformed plants,
wherein said heterologous sequence comprises a nucleic acid molecule that encodes one or more *Arabidopsis* non host resistance protein sequences selected from the group consisting of: SEQ ID NOs: 2, 4, and 6.

3. A method for conferring or improving *Fusarium* resistance in a plant, said method comprising:
transforming said plant with a nucleic acid molecule comprising a heterologous sequence operably linked to a promoter that induces transcription of said heterologous sequence in a plant cell; and
regenerating stably transformed plants, wherein said heterologous sequence comprises a nucleic acid molecule that encodes one or more *Arabidopsis* non host resistance protein sequences selected from the group consisting of:
(a) a nucleotide sequence comprising the sequence set forth in SEQ ID NO: 1, 3, or 5;
(b) a nucleotide sequence comprising at least 50 contiguous nucleotides of the sequence of SEQ ID NO: 1, 3, or 5; wherein said nucleotide sequence encodes a protein with non host *Fusarium* resistance;
(c) a nucleotide sequence having at least 90% sequence identity to the sequence of SEQ ID NO: 1, 3, or 5 and encoding the protein sequence of SEQ ID NO: 2, 4, or 6; and
(d) a nucleotide sequence that encodes the protein sequence of SEQ ID NO: 2, 4, or 6.

4. The method of 2, wherein said plant is a dicot.

5. The method of 2, wherein said dicot is soybean.

6. A method for conferring or improving *Fusarium* resistance of a plant, said method comprising:
stably introducing into the genome of a plant, at least one nucleotide construct comprising a non host resistance nucleic acid molecule operably linked to a heterologous promoter that drives expression in a plant cell, wherein said nucleic acid molecule encodes a polypeptide selected from the group consisting of: SEQ ID NOs: 2, 4, and 6.

* * * * *